(12) United States Patent
Graham et al.

(10) Patent No.: US 8,189,187 B2
(45) Date of Patent: May 29, 2012

(54) MONOLITHIC OPTICAL FLOW CELLS AND METHOD OF MANUFACTURE

(75) Inventors: Marshall Donnie Graham, Nicholasville, KY (US); William Gerry Graham, Nicholasville, KY (US); James P. Clarkin, Scottsdale, AZ (US); Mark A. Wells, Davie, FL (US); Jose M. Cano, Miami, FL (US); Carlos Alberto Arboleda, Miami, FL (US); Armando Jose Sanchez, Miami, FL (US)

(73) Assignee: Beckman Coulter, Inc., Brea, CA (US)

( * ) Notice: Subject to any disclaimer, the term of this patent is extended or adjusted under 35 U.S.C. 154(b) by 252 days.

(21) Appl. No.: 12/617,897

(22) Filed: Nov. 13, 2009

(65) Prior Publication Data
US 2010/0290041 A1    Nov. 18, 2010

Related U.S. Application Data

(60) Provisional application No. 61/114,544, filed on Nov. 14, 2008.

(51) Int. Cl.
*G01N 1/10* (2006.01)
(52) U.S. Cl. .................................................... 356/246
(58) Field of Classification Search .................. None
See application file for complete search history.

(56) References Cited

U.S. PATENT DOCUMENTS

| | | | |
|---|---|---|---|
| 4,286,873 A | 9/1981 | Carson | |
| 4,575,424 A | 3/1986 | Allington et al. | |
| 4,673,288 A * | 6/1987 | Thomas et al. | 356/72 |
| 4,786,165 A | 11/1988 | Yamamoto et al. | |
| 5,125,737 A | 6/1992 | Rodriguez et al. | |
| 6,052,184 A * | 4/2000 | Reed | 356/338 |
| 6,111,398 A | 8/2000 | Graham et al. | |
| 6,332,540 B1 | 12/2001 | Paul et al. | |
| 2001/0035947 A1 | 11/2001 | Fry et al. | |
| 2004/0095574 A1 | 5/2004 | Turner et al. | |
| 2005/0036140 A1 | 2/2005 | Elster et al. | |
| 2005/0180885 A1 | 8/2005 | Tateishi et al. | |
| 2008/0223154 A1 | 9/2008 | Kondo et al. | |

FOREIGN PATENT DOCUMENTS

JP    62-168033    7/1987

OTHER PUBLICATIONS

International Search Report and Written Opinion for PCT Application No. PCT/US2009/064201, mailed Jan. 29, 2010.

* cited by examiner

*Primary Examiner* — Tu Nguyen
(74) *Attorney, Agent, or Firm* — K&L Gates LLP; Louis C. Cullman; Thomas A. Turano

(57) ABSTRACT

An improved optical flow cell adapted for use in a flow cytometer for differentiating formed bodies (e.g., blood cells). Manufactured from a monolithic transparent material, the improved flow cell has an internal flow channel of polygonal transverse cross-section through which prepared samples can be metered and an external envelope suited to acquisition of optical parameters from formed bodies in such samples. Preferably, such flow cell is formed by a glass-drawing process in which a relatively large glass preform having a rectilinear internal channel of a desired polygonal cross-sectional shape is heated and drawn to achieve a desired cross-sectional area of reduced size. Also disclosed are preferred methods for differentiating formed bodies using the flow cell of the invention.

19 Claims, 13 Drawing Sheets

MONOLITHIC OPTICAL FLOW CELLS AND METHOD OF MANUFACTURE

CROSS-REFERENCE TO RELATED APPLICATIONS

This application is a non-provisional application claiming the benefit under 35 U.S.C. §119(e) of U.S. Provisional Application No. 61/114,544, filed on Nov. 14, 2008, which is incorporated herein by reference in its entirety.

BACKGROUND OF THE INVENTION

1. Field of the Invention

This invention relates generally to apparatus and methods for differentiating constituent types of formed bodies (e.g., cells or other small particles) in liquid samples (e.g., whole blood or other particle-suspending liquids). More particularly, this invention relates to improvements in optical flow cells of the type commonly used in flow cytometers (e.g., hematology and fluorescence flow cytometer instruments) that function to sense, differentiate, and characterize formed bodies by various optical transduction means, preferably in combination with non-optical parameters acquired via the Coulter Principle. The invention further relates to improvements in methods for making optical flow cells, by which a flow channel of polygonal cross-section is provided within a monolithic transparent element.

2. Discussion of the Prior Art

It is common practice to automate analyses of patient body fluids as an aid in diagnosing a patient's state of health. Such analyses typically include flowing a prepared portion of such body fluids through a transducer to derive certain parameters characteristic of the several different types or subpopulations of constituent formed bodies therein, differentiating and enumerating the several types or subpopulations of the formed bodies on the basis of the derived parameters, and processing or correlating the resultant information to provide desired diagnostics. For example, these tasks can be accomplished for whole blood via characterization of blood cells therein by conventional automated hematology analyzers and flow cytometers.

The fundamental performance limit of instruments of the type noted above originates in the transduction of formed-body properties into the characterizing parameters used to assign individual formed bodies to specific subpopulations. For many applications, optical transductive methods alone provide effective means for characterizing formed bodies. In these applications, a portion of a prepared sample is interrogated with optical radiation as it flows through a channel formed in an optically transparent element, or flow cell, forming a portion of an opto-electric transducer. Suitable photodetectors, also forming part of the transducer, are positioned to detect various optical parameters from an irradiated formed body, including, for example, its optical absorbance of the interrogating beam, its fluorescence at different wavelengths, and its light-scattering effect within one or more angular ranges. In these optical-only applications, it will be appreciated that the physical extent of the flow-cell channel can be relatively large without adversely affecting the determination of these optical parameters. However, in other cytometric applications where such optical parameters are combined with simultaneously determined non-optical parameters, in particular those based on the Coulter Principle (discussed below), the transverse cross-section and length of the flow-cell channel must be dramatically restricted to achieve suitable signal strength.

Due to the low sensitivity of then-existing optical sensing methods, W. H. Coulter devised an electronic method for characterizing minute formed bodies suspended in a liquid. The now well-known Coulter Principle enables determination of the volume of formed bodies, by flowing a sample portion prepared in an electrically conductive liquid through a particle-sensing (or volumeter) conduit simultaneously with an electric current. The electrical resistivity of the particle-suspending liquid differs from that of the particles, the electrical contrast permitting counting and sizing of particles transiting the volumeter conduit. Although other geometries were discussed in Coulter's U.S. Pat. No. 2,656,508, volumeter conduits are usually cylindrical bores in a thin insulative wafer, the conduit's cross-sectional area and length determining volumetric sensitivity, coincidence volume, and maximum passable formed-body dimension; thus, conduit diameters are typically at most an order of magnitude greater than the diameter of the typical formed bodies to be analyzed. The volumeter conduit forms the only fluidic communication between two insulative chambers, with no requirement on the optical characteristics of the wafer material surrounding the conduit. Typically, a direct current (DC) is provided through the conduit, and resistive Coulter volume (V) signals are acquired via a pair of electrodes positioned outside the opposite ends of the volumeter conduit. However, in U.S. Pat. No. 3,502,974 to W. H. Coulter and W. R. Hogg, an excitation current including at least one alternating current (AC) was provided through the conduit, thereby permitting determination of not only the resistive but also reactive components of the conduit current resulting from its modulation by passage of a formed body. When such currents include one having a frequency in the radio-frequency (RF) range (e.g., 23 MHz), the respective components permit estimation of the volume (V) and electrical conductivity (C) of a formed body, and the ratio of the reactive to resistive components is said to be the "opacity" of the formed body.

In commonly assigned U.S. Pat. No. 6,228,652 (hereinafter, the '652 patent), apparatus is disclosed that can provide simultaneous acquisition of various optical, Coulter V, and Coulter C signals from an individual formed body, with subsequent differentiation of formed-body subpopulations in whole blood based thereon. In the '652 patent the preferred flow-cell comprises an optically transparent element having a prismatic exterior envelope of square transverse cross-section, measuring about 4.2 mm on each side, and having a length of about 6.3 mm. (As used herein, the word "prismatic" refers to any three-dimensional figure composed of three or more intersecting sides that are planar, and a pair of opposing ends that are polygonal in shape. "Polygonal" is used herein to refer to any closed plane figure having at least three substantially straight sides, and "planar" as used herein refers to a surface having an area that is predominantly flat.) Centrally located within such prismatic element is a prismatic volumeter conduit having a square transverse cross-section about 50 micra on each side and a length of about 65 micra; the relatively small transverse cross-section and length of the conduit are necessary to attain a reasonable volumetric sensitivity and coincidence volume for acquiring said V and C signals. Thus, the ratio of the respective transverse cross-sectional areas of said conduit and envelope is approximately 0.00014, and the wall thickness is about 2.075 mm. To acceptably limit aberrational content of optical signals, surfaces of the prismatic envelope and conduit must be substantially parallel, with optical planarity. This combination of square/square cross-sectional geometries, wall thickness, wall surface parallelism, and wall flatness is difficult to achieve.

To manufacture prismatic flow cells of the type described in the '652 patent, a relatively complex planarization process has been used wherein four transparent plates, e.g., a form of silica ($SiO_2$, commonly called quartz), are polished to predetermined thickness and finish and assembled as shown in FIG. 13. During assembly, a pair of said plates CC1 and CC3 is spaced apart by the other pair CC2 and CC4 to form two walls of flow cell 30, with the pair of equal-thickness spacer plates appropriately spaced apart a predetermined distance so that their opposing edges complete an internal channel Z. Preferably, these separate complementary elements are of appropriate dimensions and joined at their interfaces by a fusion technique to form a prismatic rod having an internal, longitudinally-extending, straight channel of a desired square transverse cross-section therein. This rod is then cut to a desired length, e.g., 6.3 mm, and polished to the desired external geometry and dimensions to form a flow cell having a prismatic envelope, e.g., opposing sides 50 in FIG. 13 having a flat-to-flat separation of 4.2 mm. Such flow cells having prismatic flow channels of constant longitudinal section but various cross-sections, both square and rectangular, have been made by varying the thickness and separation of the two spacer plates separating the two windows. A prismatic volumeter conduit, e.g., the 50 micra by 50 micra square conduit described above, is formed in such flow cells by boring the square channel from both ends to a suitable diameter (e.g., 1.25 mm), leaving in situ a short length (e.g., 65 micra) of the original channel in the middle of the flow cell that opens at each end into a small cup-shaped recess (e.g., of radius about 600 micra) substantially tangent to a 90-degree cone coaxial with the original channel and continuous with the end bores. The resulting longitudinal channel section is such that the sample liquid in a hydrodynamically-focusing sheath liquid passes centrally through the volumeter conduit within the flow cell. Other embodiments of flow cells made by the planarization process have been adapted to function in fluorescence flow cytometers such as the XL and FC500 research analyzers, as well as the Altra™ cell sorter, all made and sold by Beckman Coulter, Inc. (Single-piece flow cells suited to application in these instruments and made by the method of the present invention are illustrated in respective FIGS. 9, 10, and 11 and will be discussed as embodiments.)

Although useful prismatic flow cells have been produced by the above-described planarization process, the yield of reliably functioning flow cells processed to contain a volumeter conduit has proven to be very low, typically less than 1 in 3. For formed bodies transiting the internal volumeter conduit Z of useful flow cells (e.g., BC2 in FIG. 13), optical signals acquired through the two windows may be substantially repeatable (e.g., the forward scatter (FS) signals resulting from a sensor placed outside window CC1 and on the optical axis OA opposite the entry window CC3 for radiation beam B in FIG. 13). However, those acquired through the two walls comprising spacer plates (e.g., fluorescence (F) signal acquired through CC2 and side-scatter (SS) signal acquired through CC4 in FIG. 13) demonstrate both sensitivity to excitation beam position in individual cases and unit-to-unit variability in the resulting optical signals. More importantly, flow cells made by the planarization process (e.g., flow cell 30 in FIG. 13) are prone to subsequent failure modes: Firstly, irregularities and air pockets in the fused joins characteristic of the planarization approach result in localized heating due to the RF component of the conduit excitation current, with consequent failure of the join; secondly, some flow cells demonstrating longevity under RF exposure show join-dependent unit-to-unit variability in optical signals, even though joins are systematically positioned relative to the axis of optical excitation; thirdly, join imperfections tend to enlarge when sample flows are accompanied by significant cyclic pressure; and finally, flow cells left in stored apparatus tend to separate along the joins due to crystallization of salts if residual reagents are allowed to evaporate.

More-complex production processes, wherein various transparent solids of predetermined geometry are appropriately assembled, have also been used to make optical flow cells having prismatic volumeter conduits of a desired geometry and dimensions. Commonly assigned U.S. Pat. No. 4,348,107 (hereinafter the '107 patent) discloses optical flow cells in which a volumeter conduit having a preferably square transverse cross-section is contained within an envelope having an exterior spherical surface or other surface of revolution. (Single-piece flow cells having this envelope, but made by the method of the present invention, are illustrated in FIGS. 12A, 12B, and 12C and will be discussed as embodiments.) As illustrated in the '107 patent, such flow cells are made by joining together four complementary, truncated, square-based pyramids formed in a transparent material (e.g., quartz). The apex is polished from each pyramid to a depth calculated to yield one side of the desired volumeter conduit, and the pyramids then appropriately assembled and adhesively joined together so that the truncated apexes form an unobstructed square prismatic conduit, the adjacent faces of the joined pyramids forming a tapering longitudinal section at one or both ends of the conduit. Although optical signals may be acquired through the planar walls of the resulting prismatic envelope, it is preferred that means unspecified in the '107 patent then provide the flow cell an envelope formed as a surface of revolution. An extension allowing coupling of the sample liquid and a hydrodynamically-focusing sheath liquid through the conduit is sealed to the resulting flow cell where its surface is intersected by one or both the approaches formed by the exposed sides of the four pyramids. The '107 patent notes that optical and mechanical characteristics of said structure proved suboptimal, the adhesive joins potentially fluorescing or separating, but provides no alternative joining method. A theoretical comparison, of the optical properties of the idealized '107 flow-cell structure with those of a flow cell having a square transverse cross-section in a square prismatic envelope, was published in *Applied Optics* (26:3244-3248, 1987) by the inventor and one of the present co-inventors; no method for production of either flow-cell structure was described. The inventor and other co-workers later verified some of those theoretical predictions in a second comparison (*Cytometry* 20:185-190, 1995) using an embodiment of the '107 flow cell having the four pyramids fused together, thus avoiding said adhesive join problems, and a monolithic cylindrical flow cell such as used in automated hematology instruments manufactured and sold by Beckman Coulter, Inc. (discussed below); FIG. 2 in this publication shows the '107 flow cell sealed, after production of a polished spherical exterior envelope, between extensions of the plastic chambers housing electrodes enabling acquisition of Coulter V and C signals. As disclosed in U.S. Pat. Nos. 4,673,288 and 4,818,103, variations of the approach disclosed in the '107 patent have been used to provide prismatic volumeter conduits having a triangular cross-section in a similarly shaped envelope, with square, five-sided, etc., structures said to be within the scope of the invention. To allow efficient collection by a microscope objective of optical signals from such triangular volumeter conduits, in U.S. Patent Application 2007/0085997 a thin transparent plate (window) is substituted for one of the truncated pyramids, with the envelope completed by the remaining two complementary components modified to facilitate interrogation of formed bodies by optical radiation through their walls; this approach is implemented in the Quanta™ cytometer sold by Beckman Coulter, Inc. As will be appreciated, multiple joins, subject to the same disadvantages as those occurring in the above-described planarization process, are required in flow cells including a plurality of such fused elements. Further, the demands of machining the apexes from multiple elements, assembling the elements together, and joining them to attain repeatable polygonal conduits having the desired conduit dimensions make this approach both more costly and even less attractive as a production process. This approach becomes increasingly disadvantageous as the number of prismatic faces increases.

In characterizing various types of formed bodies by cytometric techniques, a recurring need is to simultaneously acquire several different types of optical signals resulting from interaction of the formed bodies with one or more radiation sources, i.e., some selected combination of multiple-wavelength fluorescence (F) signals, absorption (A) signals, and scatter (S) signals such as forward-scatter (FS), side-scatter (SS), or back-scatter (BS) signals; in such applications, the four external faces on a square/square prismatic flow cell requires that a plurality of sensors view an interrogation zone through complex beam-splitting and/or wavelength differentiating optics which, in addition to adding cost, introduce alignment and other optical difficulties. One might address this problem by adding more faces to the prismatic envelope and volumeter conduit of the flow cell, whereby both the flow cell envelope and internal conduit might have a pentagonal, hexagonal, heptagonal, etc., transverse cross-section, so that each optical measurement of interest could be made through a separate face of the flow cell. However, the manufacture of such prismatic flow cells by any of the above-noted conventional techniques would be so complex and time-consuming as to be totally impractical, especially if such flow cells were to be made in relatively large numbers for incorporation into commercial cytometric instruments.

It is known in the glass-working art to draw tubing from a larger preform of various inner and outer diameters between which is a cylindrical wall up to several centimeters in thickness. During the drawing operation, the preform is heated to a predetermined temperature at which its viscosity permits deformation, whereupon it is drawn axially, usually in a vertically downward direction, at a constant and predetermined rate. During this process, the diameters of the inner and outer cross-sections of the preform are substantially reduced with the original circular shapes being substantially retained, such shapes being the minimum energy shape, and the wall of the preform is significantly reduced in thickness. This drawing process has been adapted to form thick-wall transparent $SiO_2$ tubing for use in producing single-piece (monolithic) flow cells, e.g., those used in the Coulter® Model LH750 automated hematology instruments as described in commonly assigned U.S. Pat. No. 5,125,737 (hereinafter the '737 patent) and manufactured and sold by Beckman Coulter, Inc. After a preform is drawn to a preferred inner diameter (e.g., 50 micra), the tubing is cut to a preferred length (e.g., about 6 mm), and a suitable flat (e.g., 1 mm wide) is lapped on the outer cylindrical surface of the tube which, as a result of the drawing has been reduced to a diameter of about 3.5 mm. The flat provides an optical port through which a radiation beam (e.g., from a HeNe laser) can be coupled, along a diameter, to the central cylindrical channel in the drawn tube. The flat is made substantially parallel to the channel axis at an arbitrary location on the outer cylindrical surface, e.g., to avoid an objectionable optical defect in the wall. The cylindrical channel is partially enlarged by boring from both ends to a suitable diameter (e.g., 1.25 mm), leaving in situ a short length (e.g., 65 micra) of the original channel in the middle of the flow cell that opens at each end into a small cup-shaped recess (e.g., of radius 600 micra) substantially tangent to a 90-degree cone coaxial with the original channel and continuous with the end bores. In use, the length of the original channel in the longitudinal section thus formed functions as a Coulter volumeter conduit, and the cylindrical bores communicate with external electrode chambers in a supporting structure, whereby the sample liquid in a hydrodynamically-focusing sheath liquid can be made to pass centrally through the volumeter conduit. Coulter V and C signals are acquired from the electrodes as formed bodies pass through the volumeter conduit; meanwhile, forward-scatter (FS) signals from the radiation beam are simultaneously acquired from the individual formed bodies as they pass through the cylindrical volumeter conduit.

Optical flow cells of the above type, i.e., truly monolithic flow cells made from a joinless, single piece of transparent material, inherently avoid many of the limitations and disadvantages described above for composite flow cells comprising joined transparent components of complementary geometries. Forward-scatter (FS) signals acquired from such flow cells permit reliable differentiation and enumeration of individual formed bodies when suitably correlated with Coulter V and C signals. However, because both the optically transparent envelope and the central interior volumeter conduit of such flow cells exhibit a substantially circular transverse cross-section, the wall of such flow cells acts as a non-axisymmetric lens, and scatter (S) signals acquired through it incur substantial optical aberrations that limit the ability to differentiate between certain types of formed bodies. While such differentiation can be improved by adding fluorescence (F) signals at different wavelengths, e.g., by selectively tagging the formed bodies with fluorescent dyes or dye-bead conjugates, such F signals are even more disadvantageously affected by optical aberrations than are the various scatter signals. Consequently, extensive effort has been directed toward flow cells having a prismatic channel surrounded by planar walls such as in the square/square geometry disclosed in the above '652 patent or for the triangular volumeter conduit disclosed U.S. Patent Application 2007/0085997 and its precursors, whereby such optical aberrations may be reduced. As noted, however, such flow cells are both difficult to produce using conventional production methods and subject to failure over time. Thus, although others have proposed flow cells within which such simultaneous optical, or optical and Coulter, measurements may be made on individual formed bodies flowing through a prismatic channel, no one has either reduced to practice a truly monolithic (i.e., joinless single-piece) flow cell suited to such applications or provided a technically enabling disclosure for doing so.

SUMMARY OF THE INVENTION

In view of the foregoing discussion, an object of this invention is to provide an improved method for making optical flow cells in which the interior flow channel is prismatic, a method that provides a significantly improved yield of useful flow cells manufactured that are less subject to failure over time, and a method that provides flow cells enabling better differentiation of various types of formed bodies.

Another object of this invention is to provide a truly monolithic (joinless) optical flow cell in which the transverse cross-section of the internal flow channel has a transverse cross-section that is polygonal.

Still another object of this invention is to provide an improved method for cytometrically differentiating various types of formed bodies using an optical flow cell having at least three planar windows through which various optical parameters of formed bodies passing through the prismatic channel of the flow cell may be derived.

Yet another object of this invention is to provide an improved method for cytometrically differentiating various types of formed bodies using an optical flow cell having at least three planar windows through which various optical parameters of formed bodies passing through the prismatic channel of the flow cell may be derived and in a portion of the channel of which at least one of the Coulter volume (V) and conductivity (C) parameters is detectable.

The inventions described and claimed herein are based on the discovery that the tube-drawing art used to provide thick-walled flow cells having cylindrical transverse cross-sections in both internal channel and external envelope can be adapted for use in making monolithic optical flow cells having a flow channel with a non-circular, preferably polygonal, cross-section. It was highly unexpected that the geometry of a desired non-circular (e.g., polygonal) cross-section of a relatively large channel centrally formed in a cylindrical preform could be maintained during a heating and drawing operation in which the cross-sectional area of the preform channel is shrunk by a factor of at least 1,000:1 to produce a polygonal flow channel of the size required for the cytometric analysis of formed bodies such as blood cells.

A preferred method for making an optical flow cell of the above type comprises the simultaneous steps of heating and drawing a preform of transparent material, most preferably synthetic amorphous silica (i.e., silicon dioxide, $SiO_2$). The preform comprises a cylindrical tube of such material having a central, axially-extending channel exhibiting a substantially uniform transverse cross-section of a desired polygonal shape, e.g., triangular, rectangular, or hexagonal. Less desirably, the preform is a rod of suitable dimensions formed via the above-described planarization process. The preform preferably has a flat formed on its cylindrical outer surface, such flat being formed substantially parallel to one of the planar surfaces of the interior polygonal transverse cross-section of the channel. The preform is heated to a predetermined temperature above the glass softening temperature, and it is drawn at a controlled rate, for a controlled time and at a constant angular orientation, whereby the polygonal shape of the internal channel is maintained during the drawing operation, the parallelism between the external flat and the planar surface of the polygonal flow channel is maintained, and the desired flow channel dimensions after cooling are achieved. After the drawn tubular structure is cooled and cut to a desired length, the flat on the outer surface is used as a reference surface, whereby an optical planar surface may be lapped at a predetermined angle to said flat and substantially parallel to one of the planar surfaces of the interior polygonal flow channel. An envelope comprising a plurality of planar surfaces is lapped on the outer surface of the drawn structure, by using the first optical surface as a reference surface against which the angle of the additional surfaces are measured, whereby the outer envelope of the drawn structure can be made of a polygonal cross-section that is similar in shape to the interior channel, is substantially coaxial therewith, and has sides substantially parallel thereto. Alternatively, an envelope comprising a non-cylindrical surface of revolution may be ground and polished on the outer surface of the drawn structure such that a residual portion of said flat may be lapped substantially parallel to one of the planar surfaces of the interior polygonal flow channel, thus forming a planar window in the surface of revolution. Less desirably, the flat on the cylindrical outer surface of the preform may be omitted and the outer surface of the drawn structure lapped to provide a planar reference surface, e.g., preferably extending substantially parallel to one of the planar surfaces of the interior polygonal flow channel, said reference surface then being used to lap additional planar surfaces on the outer surface of the drawn structure or to form a planar window in a surface of revolution in the aforesaid manner.

According to another aspect of the invention, an improved optical flow cell is provided for use in a flow cytometer of the type adapted to characterize small particles on the basis of at least their respective optical properties. Such a flow cell comprises a monolithic structure of optically-transparent material. Preferably, the monolithic structure is produced by a heating/drawing process. A portion of such monolithic structure defines a prismatic channel through which formed bodies can be made to pass while being irradiated by optical radiation passing through the structure. At least an axial portion of such flow channel has a transverse cross-section of polygonal shape, whereby optical radiation enters the flow channel to irradiate formed bodies within the flow channel, and optical radiation resulting from said irradiation exits from the flow channel at different angles through planar surfaces or through a non-cylindrical surface of revolution coaxial with said flow channel. Preferably, the polygonal cross-section of the internal flow channel has three to eight sides. In a preferred embodiment, the envelope of the monolithic structure is also prismatic in shape, with the number of prism sides being equal to the number of sides of the flow channel and substantially parallel thereto, whereby a plurality of flat windows is provided through which radiation can enter and exit the flow channel. Alternatively, to enable radiation to exit the flow cell with minimal deviation due to refraction at the envelope boundary, an envelope comprising a non-cylindrical surface of revolution may be ground and polished on the outer surface of the drawn structure, and if said envelope is provided an appropriate flat substantially parallel to one of the planar surfaces of the interior polygonal flow channel, radiation may be advantageously coupled to the flow channel through a planar window.

A preferred method for differentiating formed bodies using the flow cell of the invention comprises the steps of (a) providing a monolithic flow cell of the type described herein having an internal flow channel of polygonal transverse cross-section and having an envelope comprising at least five discrete walls; (b) passing formed bodies through the polygonal flow channel while irradiating such formed bodies with a beam of radiation passing through one of such walls; (c) detecting forward-scatter (FS) signals from the irradiated formed bodies through a second of such walls; (d) detecting fluorescence (F) signals from the irradiated formed bodies through at least a third of such walls; (e) detecting side-scatter (SS) signals from the irradiated particles through a fourth wall; and (f) detecting back-scatter (BS) signals from the irradiated formed bodies through a fifth of such walls. Alternatively, such optical signals may be acquired in a corresponding manner via plurality of separate sensors appropriately positioned around such a monolithic flow cell comprising a non-cylindrical surface of revolution rather than planar walls. Preferably, at least some of the above optical measurements are combined with at least one of Coulter volume V and conductivity C measurements, made simultaneously on the irradiated formed bodies passing through the flow channel, to differentiate such formed bodies.

The invention and its various advantages will be better appreciated from the ensuing detailed description of preferred embodiments, reference being made to the accompanying drawings.

DETAILED DESCRIPTION OF PREFERRED EMBODIMENTS

Flow cytometers acquire diagnostically important data from samples of patient body fluids containing various formed bodies, and many different embodiments have been developed. All depend on a channel in a flow cell through which such samples may be passed after undergoing various preparatory protocols and in which various properties of the formed bodies may be sensed, whereby the several types of subpopulations of formed bodies therein may be differentiated and enumerated and the derived parameters processed and correlated to provide desired diagnostics. As discussed above, flow cytometers incorporating simultaneous acquisition of optical and Coulter V and/or C parameters from an individual formed body require within the flow channel of their optical flow cells a constriction (or volumeter conduit) having relatively small lengths and transverse cross-sections. One such hematology analyzer is more fully disclosed in the above-noted U.S. Pat. No. 6,228,652, on which two of the present co-inventors are co-inventors and the disclosure of which is incorporated herein by reference. Briefly, the analyzer is of the type that operates to automatically sense, differentiate, and count various types of formed bodies (e.g., blood cells, platelets, etc.) contained in different samples of patient body fluids and to report its findings.

Figure 1:
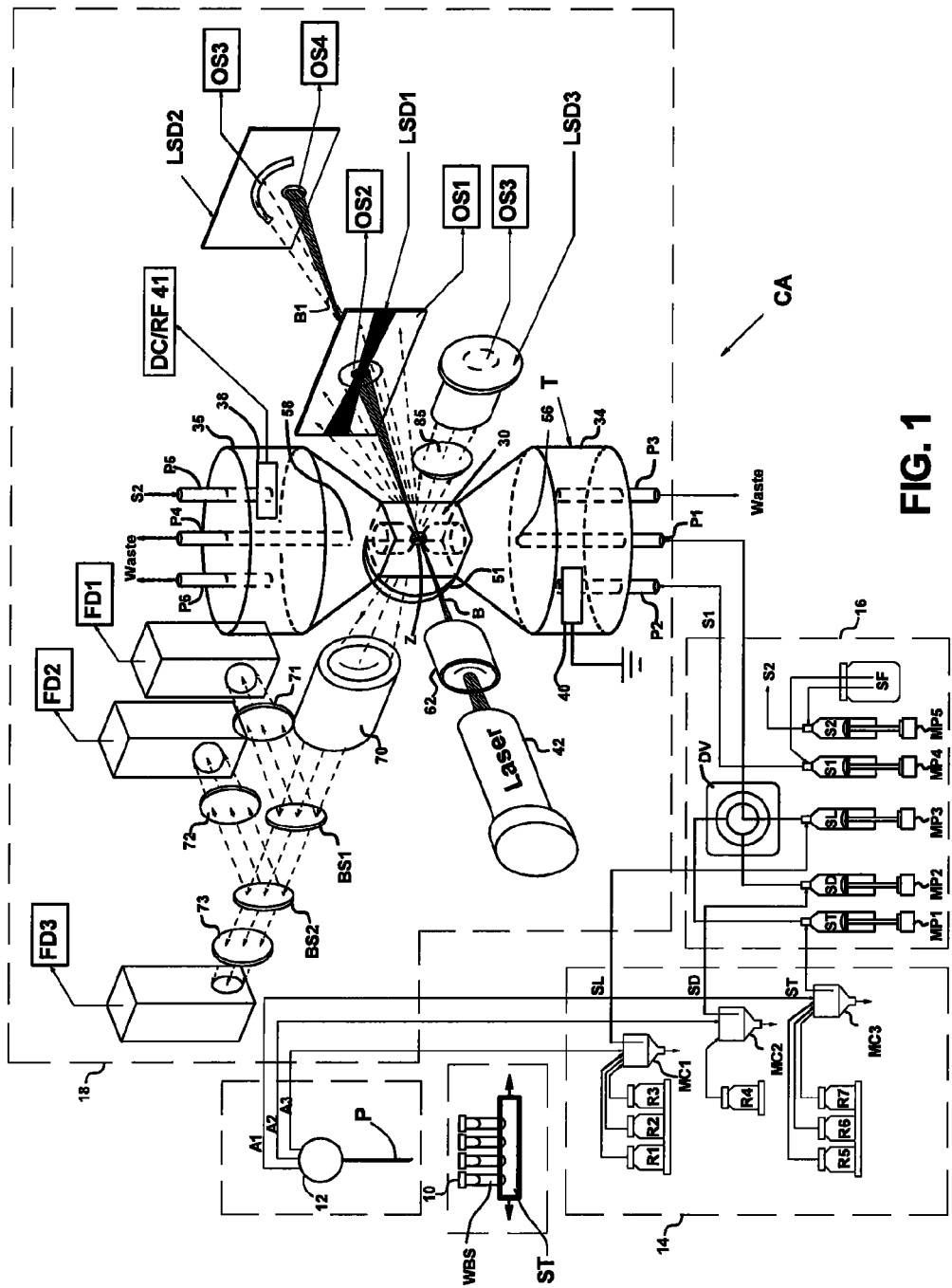
FIG. 1 is a schematic illustration of the sample-processing and data-acquisition portions of a flow cytometer incorporating a preferred embodiment of a four-sided monolithic optical flow cell structured and manufactured in accordance with the method of the invention.

Referring now to the drawings, in which for clarity all internal sample passageways are shown enlarged and out of proportion with respect to external flow-cell envelopes, FIG. 1 schematically illustrates the sample-processing and data-acquisition portions of such an analyzer CA that is distinguished from prior-art analyzers in comprising an improved monolithic optical flow cell 30 (better shown in FIG. 2) structured and manufactured in accordance with the present invention. As illustrated, optical flow cell 30 is the central component of the analyzer's opto-electric transducer assembly T that operates to optically and electrically interrogate each formed body in a patient sample to be analyzed. The patient samples (e.g., whole blood samples WBS) are presented to the analyzer in different test tubes or vials 10 that are moved within the instrument by a sample transport ST. Upon presentation of such vials to an aspiration probe P, a predetermined volume of sample is aspirated from each. Each aspirated sample is segmented by a conventional blood-sampling valve 12 to produce a plurality of aliquots (e.g., A1-A3) that are then dispensed to different mixing chambers (e.g., MC1-MC3) within a sample-preparation component 14 of the analyzer. While in the mixing chambers, each aliquot is mixed with one or more reagents (e.g., R1-R7) adapted to selectively react with and/or dilute certain types of formed bodies in the sample. Sample-preparation component 14 can produce, for example, a lysed and stained sample, $S_L$, comprising predominantly white blood cells and other cells (e.g., nucleated red blood cells) that have been stained with a fluorescent dye; a diluted and stained sample, $S_D$, containing all blood cell types in a highly diluted suspension, some of such cells (e.g., the reticulocyte subset) being stained with a fluorescent dye; and a lysed and tagged sample, $S_T$, comprising predominantly white blood cells in a suspension, including selected white cells (e.g., CD4 and CD8-positive cells) that have been stained or otherwise labeled, e.g., via a monoclonal antibody, with a fluorochrome or fluorescent particle. Precisely metered volumes of each of the prepared samples, as provided by a metering mechanism 16, are then selected by a conventional distribution valve DV and pumped (e.g., by metering pumps MP1, MP2, or MP3) through sample input port P1 of the analyzer's opto-electric transducer assembly T in transducer component 18; and metering pumps MP4 and MP5, respectively, provide sheath liquid SF to port P5 of the transducer assembly T to hydrodynamically center sample flows through volumeter conduit Z of flow cell 30 and maintain a predetermined pressure differential between chambers within cap elements 34 and 35 of transducer assembly T. As will be discussed, certain optical, physical, and electrical properties of individual formed bodies or other particles in the samples are simultaneously sensed and converted to electrical signals as the samples are individually metered through volumeter conduit Z. Such signals occur as electrical pulses and are parameters of, for example, each formed body's DC volume (V) and RF electrical conductivity (C) as determined by the Coulter Principle, its absorption of radiation (A), its various light-scattering (S) properties [i.e., forward scatter (FS), side scatter (SS), and/or back scatter (BS)], and its fluorescence properties (F) at different wavelengths. Various combinations of such signals are processed by conventional cytometer components, such as disclosed in the '652 patent but not shown in FIG. 1, to provide information appropriate to correlation by algorithms providing desired diagnostic information.

Figure 2:
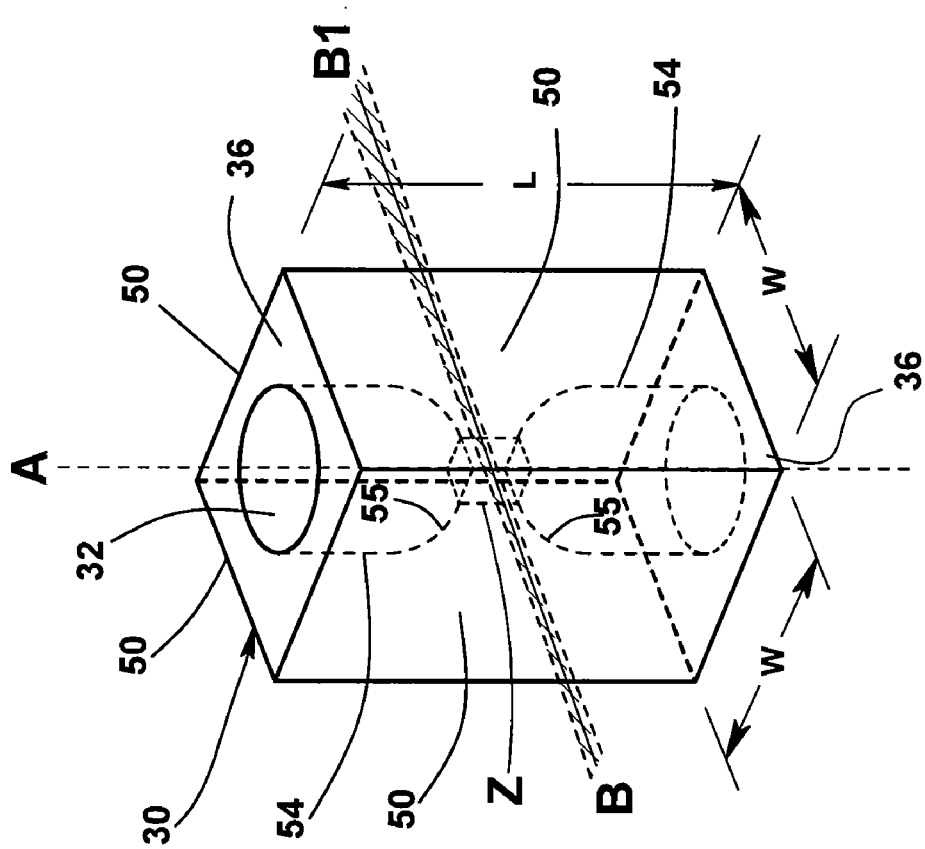
FIG. 2 is a perspective illustration of the optical flow cell used in the FIG. 1 instrument.
Figure 3:
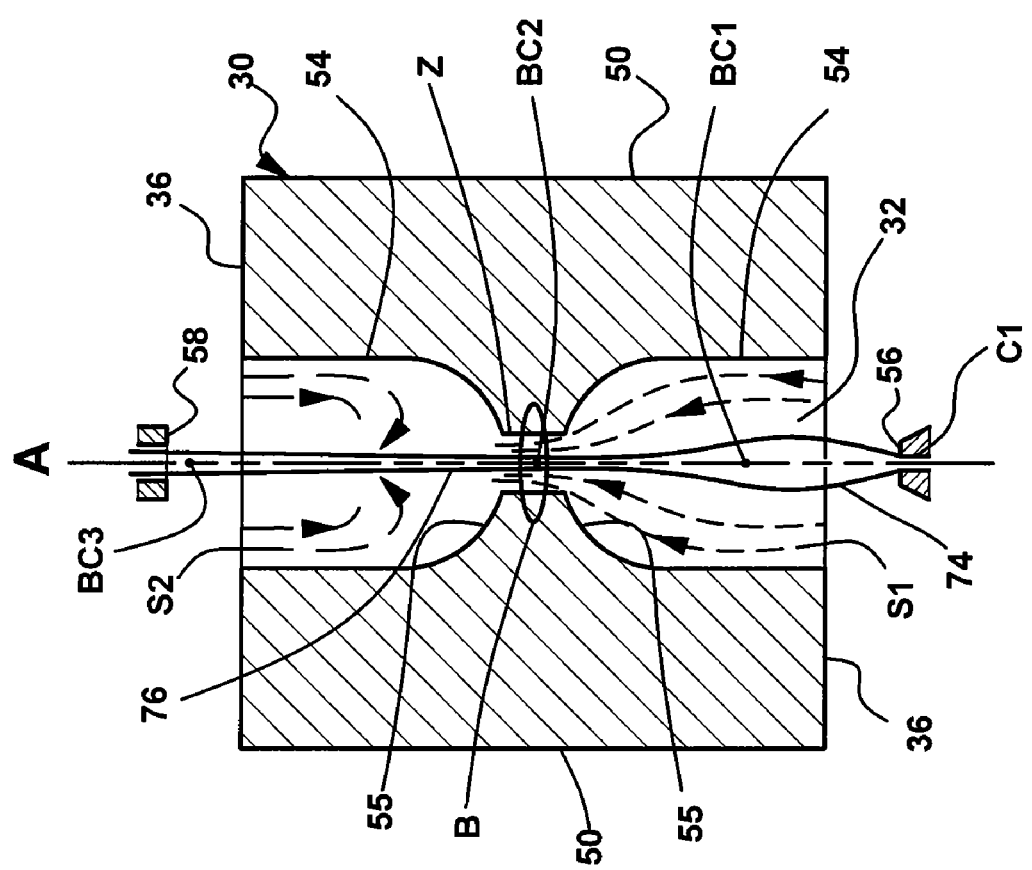
FIGS. 3 and 4 illustrate longitudinal and transverse cross sections of the optical flow cell shown in FIG. 2, FIG. 3 including the flow-cell axis and FIG. 4 being taken in a plane through the particle-sensing zone of the flow cell that parallels the flow-cell end faces.
Figure 4:
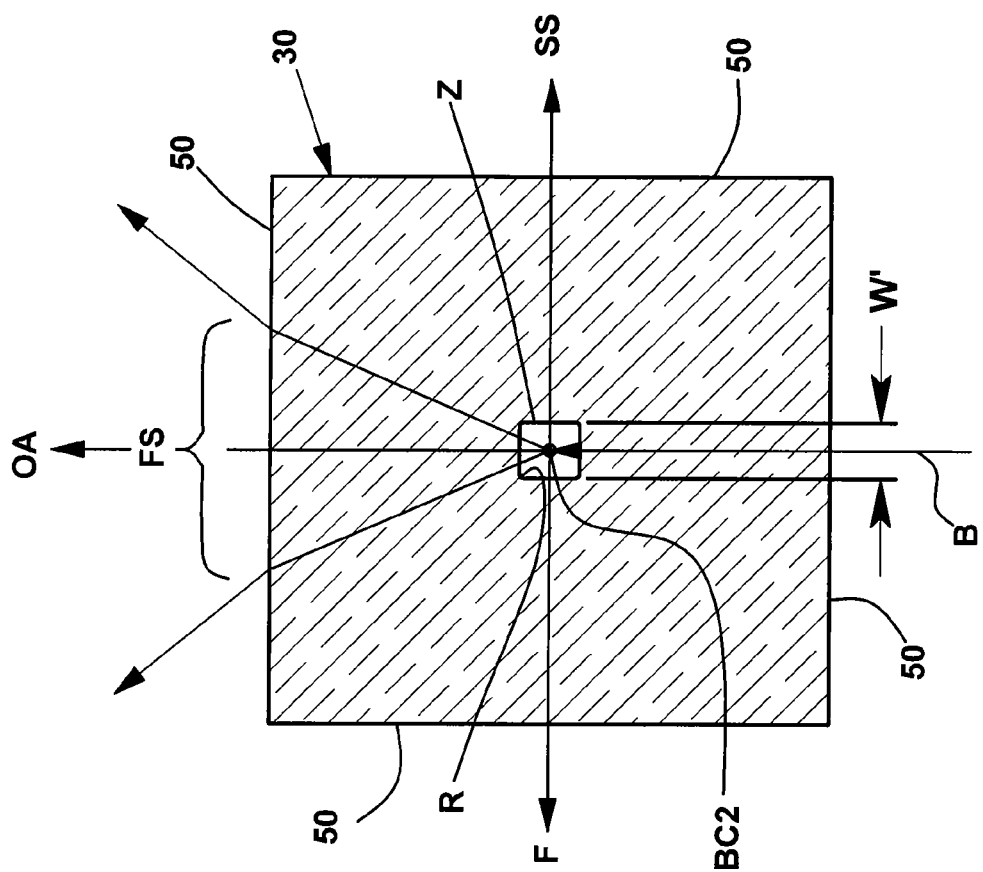

Optical flow cells, e.g., flow cell 30 in FIG. 1 fabricated in accordance with the method of the present invention, constitute the essential element in the transductive process just outlined. The improved method by which flow cell 30 is fabricated distinguishes it from prior-art flow cells and is generally applicable to a broad variety of optical flow-cell embodiments. Manufactured from a joinless (i.e., seamless), monolithic, transparent material, flow cell 30 generally comprises an internal channel through which prepared samples can be metered and having an external envelope suited to acquisition of optical parameters from formed bodies in such samples. As will be detailed below, in accordance with the invention said monolithic structure is first fabricated as an oversize preform of silica (SiO$_2$, commonly called "quartz") or most preferably of synthetic amorphous silica, so that the interior channel is bounded by three or more planar surfaces. The preform is then heated to a predetermined temperature at which its viscosity permits deformation and drawn axially at a constant and predetermined rate, whereby the transverse cross-sections of the preform and its interior channel are reduced. It has been discovered that if during such drawing operation the channel cross-section is caused to maintain a constant angular orientation with respect to the oversize preform, on cooling the drawn structure the channel's original non-circular geometry is unexpectedly retained in a substantially uniform polygonal transverse cross-section of a desired dimension, said channel being substantially rectilinear and prismatic in form. In preferred embodiments, the planar surfaces bounding such reduced interior channels have a width (e.g., W' as shown in FIG. 4) measuring between about 40 and 250 micra; if optical parameters alone can be used to characterize and differentiate the formed bodies of interest, the flow channel width is typically 100 micra or more, but if one or more Coulter parameters are desired, the flow channel width is typically 150 micra or less. In subsequent fabrication steps an appropriate segment of such drawn structure is provided with an exterior envelope appropriate to requirements of a particular application, i.e., comprising a plurality of planar optical surfaces parallel to at least some of said channel surfaces (e.g., as in FIGS. 2 through 6 and FIGS. 9 through 11) or forming a non-cylindrical surface of revolution (e.g., as in FIGS. 12A through 12C). Segments, so fabricated to provide desired envelope dimensions and optical finish, are well suited to use as flow cells in flow cytometers relying solely on optical transductive methods. The monolithic nature of flow cells so made overcomes the optical inhomogeneities, failure modes, and manufacturing disadvantages of similarly shaped, multi-component structures manufactured by aforementioned prior-art processes based on assemblage of complementary planarized plates or truncated solids. To limit aberrational effects in optical parameters associated with cylindrical monolithic flow cells, co-planar transverse cross-sections of the flow-cell envelope and of the particle-sensing portion of the internal channel may be geometrically similar polygons having sides that are substantially parallel, e.g., in FIGS. 2 and 3 the cross-sections of the envelope defined by optically polished, planar, rectangular surfaces 50 and of portion Z of passageway 32 are both substantially square, the transparent material forming the wall of flow cell 30 thus providing windows of substantially uniform thickness through which optical parameters of formed bodies transiting said sensing portion may be determined. In the embodiment therein shown, the width W of sides 50 is preferably between 2 and 8 mm, the length L of the sides is typically between 5 and 25 mm, and the length of portion Z of passageway 32 is typically between 50 and 300 micra. To provide a preferred embodiment including a particle-sensing zone suited to transduction of Coulter V and/or C parameters from formed bodies in whole blood samples, the respective width of each channel side of portion Z in passageway 32 is about 50 micra, thus providing a cross-sectional area for said portion Z of about 2500 micra$^2$ within an envelope of which the respective width W of each side 50 is about 4.2 mm and the respective length L of each side 50 is about 6.3 mm. As shown in FIGS. 2 and 3, passageway 32, extending between the opposing end surfaces 36 of flow cell 30 and typically coaxial with its longitudinal axis A, is preferably enlarged from said internal prismatic channel through end surfaces 36 to form an hour-glass shape having cylindrical bores 54 and surfaces of revolution 55 providing a smooth transition therefrom to a portion of the original channel. Preferred lengths for portion Z of original channel range between about 1.2 to 1.4 times the width of the channel side, or between about 60 and 75 micra for the present preferred embodiment, but greater lengths may be advantageous at high sample flow rates. Portion Z of the original channel thus defines in the vicinity of the axial midpoint of passageway 32 a volumeter conduit of uniform polygonal transverse cross-section within which not only the Coulter V and C parameters, but also the various optical A, S, and F parameters, of individual passing formed bodies can be simultaneously determined. As shown in FIGS. 1 through 4, a beam of optical radiation B enters and exits volumeter conduit Z through a pair of windows formed between its planar sides and planar sides 50 of flow cell 30, and optical aberrations associated with the cylindrical surfaces of aforementioned monolithic flow cells are thus avoided; in the aforesaid preferred embodiment the thickness of said windows are approximately 41 times the channel width, requiring a minimal wall thickness of about 57 times the channel width in the drawn structure used in its fabrication. End surfaces 36 of flow cell 30 in FIGS. 2 and 3 are coupled to FIG. 1 cap elements 34 and 35 which, via their internal geometry, define chambers through which both a sample to be analyzed and a sheath liquid SF, used to hydrodynamically focus or center the sample through said particle-sensing zone Z, can be coupled into passageway 32 and, following passage therethrough, appropriately flushed to waste, thereby preparing passageway 32 for analysis of a different sample.

As shown in FIG. 1, cap elements 34 and 35 are provided with a plurality of ports P1-P6 which serve to 1) introduce one or more prepared samples to be analyzed and a sheath liquid into flow cell 30, 2) drain exiting sample(s) and sheath liquid to waste, 3) flush one or both internal chambers in caps 34 and 35 to waste, and 4) provide a vacuum to prime tubing supplying the various ports. Port P1 is fluidly coupled to the metering component 16 and serves to introduce metered aliquots of sample $S_L$, $S_D$, or $S_T$ as selected by distribution valve DV to nozzle 56 for injection into passageway 32 of flow cell 30 for analysis as shown in FIG. 3. (It is understood that other sample injection methods, e.g., via the multi-port nozzle of the '652 patent, may be used in other embodiments.) Port P2 is also fluidly coupled to the metering component 16 and serves to introduce metered volumes of a sheath liquid $S_1$ to the chamber in cap element 34, such liquid serving to hydrodynamically focus or center samples in volumeter conduit Z. In FIG. 3, sample introduction nozzle 56 (which is only partially shown) has a channel C1 into which port P1 couples a precisely metered volume of sample delivered by metering component 16 of FIG. 1; said channel serves to project a stream of sample towards particle-sensing zone Z. Meanwhile, a metered volume of sheath liquid $S_1$ that has entered chamber 34, under pressure by MP4 and through port P2, flows through passageway 32. As shown in FIG. 3, sheath liquid $S_1$ uniformly surrounds the sample stream and causes the sample to flow through the center of volumeter conduit Z, thus achieving hydrodynamic focusing of the sample stream. Upon exiting volumeter conduit Z, the sample and sheath liquid are collected by FIG. 1 sample exit tube 58 (only partially shown in FIG. 3), thus preventing re-circulating formed bodies from interfering with Coulter DC volume (V) and RF electrical conductivity (C) determinations. In FIG. 3, a first blood cell BC1 is shown after exiting the channel in nozzle 56, a second blood cell BC2 is shown in the center of volumeter conduit Z and in the path of focused laser beam B, and a third blood cell BC3 is shown entering the sample exit tube 58, which is connected to waste through port P4 in FIG. 1. To control the fluid pressure in the chamber within cap 35 and thereby control the flow of sample after it exits passageway 32, said chamber is maintained full of sheath liquid $S_2$, such liquid entering through port P5 and draining to waste through port P4. Following data acquisition from each sample, transducer assembly T is prepared for a subsequent sample by flushing the chambers in caps 34 and 35 with sheath liquid, respectively, $S_1$ from MP4 into port P2 and out of port P3 and $S_2$ from MP5 into port P5 and out of port P6.

As shown in FIG. 1, within the interior chambers in cap elements 34 and 35 are respective internal electrodes 40 and 38 that are connectable to a DC/RF circuit 41. The components of such circuit operate to (a) produce DC and RF currents through passageway 32 of flow cell 30, and (b) to detect modulations in the respective DC and RF currents produced by the passage of formed bodies through particle-sensing zone Z simultaneously with the DC and RF currents, whereby the DC volume V of a formed body is determined, as well as its RF conductivity C. As more-fully described in the '652 patent, the DC/RF circuit 41 comprises a DC current source, an AC oscillator/detector operating at a RF frequency, a coupling circuit, and preamplifiers. The coupling circuit linearly combines the currents produced by the DC source and the AC oscillator/detector, and applies the combined current to the contents of passageway 32 in transducer assembly T, as previously described. Preferably, the AC component has a frequency of about 22.5 MHz. As formed bodies pass seriatim through volumeter conduit Z, the impedance of passageway 32 is altered, resulting in a modulation of the DC current as a function of the body's physical volume V (i.e., the DC volume) and a modulation of the RF current as a function of the cell's internal conductivity C. The coupling circuit separates the modulated currents such that a DC pulse signal V is conveyed to a DC preamplifier, and the modulated RF current is detected by the oscillator/detector, resulting in a pulse signal C which is conveyed to the RF preamplifier. Preferably, both Coulter V and C pulse signals are coupled to the analyzing component of the instrument, but for some applications, only one of such signals may be sufficient. Alternatively, other applications may benefit by inclusion in RF/DC circuit 41 of a plurality of AC circuits such as here described, each operating at a different frequency.

As each formed body transits volumeter conduit Z in FIGS. 1 through 4, it is irradiated by passing through a focused laser beam B of appropriate energy distribution, as provided by a suitable laser 42 and beam-shaping optics 62. Laser 42 may be one of any appropriate type, e.g. a diode laser, providing radiation suited to the application, e.g., radiation in the 635 to 640 nm wavelength range if scatter (S) parameters are of primary interest or in the 485 to 490 nm wavelength range if certain fluorescence (F) parameters are also required. Radiation (light) scattered by each formed body may be sensed by one or more light scatter photo-detectors (e.g., LSD1-LSD3) and fluorescent radiation, if any, emitted by the formed body's fluorescent stain or fluorescent label as a result of being excited by the laser radiation, may be sensed by one or more fluorescence detectors (e.g., FD1-FD3). In the longitudinal section of flow cell 30 shown in FIG. 3, said laser beam B is focused by said beam-shaping optics to provide an elliptical bi-directional Gaussian distribution of radiation centered on volumeter conduit Z with the major axis of the elliptical distribution perpendicular to the sample flow, but conventional beam-shaping optics structured to provide a focused line of uniform radiation intensity across said conduit is preferable in applications requiring small coefficients of variation in acquired optical parameters. In the cross-sectional view of flow cell 30 shown in FIG. 4, such beam enters the forward wall of volumeter conduit Z, encounters blood cell BC2 in the optical sensing zone, and causes side scatter radiation SS and fluorescent radiation F to pass through the opposing side walls of volumeter conduit Z, while forwardly scattered light FS and axially absorbed light A pass through the rear wall of particle-sensing zone Z along optical axis OA.

As noted above and as more-fully described in the '652 patent, radiation (light) scattered from focused laser beam B by formed bodies, passing seriatim through such beam within particle-sensing Z of flow cell 30 as shown in FIGS. 3 and 4, is detected by light-scatter photo-detectors, e.g., LSD1 and LSD3 in FIG. 1. Detector LSD1 is structured and located to detect light scattered in a forward direction within an angular range between approximately 9 degrees and 41 degrees of said beam's axis, referred to as median-angle light scatter (MALS). This detector has two discrete photoactive regions, OS1 and OS2, to detect forward-scattered light in the angular ranges between about 21 and 41 degrees, referred to as upper median-angle light scatter (UMALS), and between about 9 and 20 degrees, referred to as lower median-angle light scatter (LMALS). Thus, LSD1 provides three forward-scatter (FS) signals, i.e., MALS, UMALS, and LMALS. Detector LSD3 is located to detect light scattered in a direction substantially normal (i.e., at about 90 degrees±about 10 degrees) to the axis of beam B, through one of the two lateral faces of flow cell 30. Detector LSD3 preferably comprises a lens 85 which collects and directs side-scattered light onto a PIN diode OS5 or the like and provides one side-scatter (SS) signal. However, further to description in the '652 patent, LSD1 also includes a center opening through which both the laser beam emerging from flow cell 30 and light scatter at less than about 8 degrees pass unobstructed as beam B1. Photo-detector LSD2 is appropriately located behind LSD1 and has two discrete photoactive regions, OS3 and OS4, which are structured to detect light scatter at about 5.1 degrees, referred to Low Angle Light Scatter (LALS), and the near-axial attenuation in B1, referred to as Axial Light Loss (ALL). Thus, detector LSD2 provides two additional signals for analysis, i.e., a fourth FS signal, referred to as LALS, and the absorption (A) signal, referred to as ALL. It is understood that any of aforesaid sensors may be structured to respond to radiation within other angular ranges. It is also understood that, if desired, a fourth photo-detector, structured similarly to LSD1 and suitably located between beam-shaping optics 62 and flow cell 30, would provide back-scatter (BS) signals from formed bodies in particle-sensing zone Z. Free-space coupling between laser 42 and beam-shaping optics 62, between beam-shaping optics 62 and flow cell 30, and between flow cell 30 and the several photo-detectors is shown in FIG. 1, but it is understood that in some embodiments fiber-optic coupling may advantageously replace such free-space coupling between any of such-functioning elements in transducer component 18.

Fluorescent radiation results when light at an appropriate irradiation wavelength stimulates light emission from fluorescent moieties at one or more different wavelength(s); as noted above, such moieties may be attached to or inserted into various formed bodies as is known in sample-preparation protocols for use with conventional fluorescence flow cytometers. As more-fully described in the '652 patent, fluorescent radiation from such formed bodies passing through aforesaid radiation beam B in particle-sensing zone Z of flow cell 30 is collected by plano-convex lens 51. Lens 51 is preferably coupled (e.g., by an optical cement or a jell of appropriate refractive index and having minimal fluorescence) to the lateral face of flow cell 30 opposite that through which side-scattered light is detected by LSD3, such lens functioning to optically couple fluorescent radiation out of the cell-sensing zone to a second lens assembly 70 which relays it, through a network of beam-splitting dichroic mirrors BS1 and BS2 and band-pass filters 71, 72, and 73, to a plurality of fluorescence detectors FD1, FD2, and FD3, which may be photomultiplier tubes or the like. If radiation beam B originates from a laser 42 operating at, e.g., 488 nm, said network may for example be conventionally designed to couple, in the most efficient manner, light at 525 nm, 757 nm, and 695 nm to fluorescence detectors FD1-FD3. In a conventional manner, each fluorescence detector detects fluorescent radiation in such predetermined wavelength range according to the optical properties of the dichroic mirrors and filters preceding it and converts said radiation into corresponding electrical signals. It is understood that the network of beam-splitting dichroic mirrors and band-pass filters may be extended, to allow additional fluorescence detectors to provide signals at additional wavelengths from formed bodies in particle-sensing zone Z, or that in some embodiments fiber-optic coupling may advantageously replace free-space coupling between any of the optical elements in transducer component 18.

Figure 5:
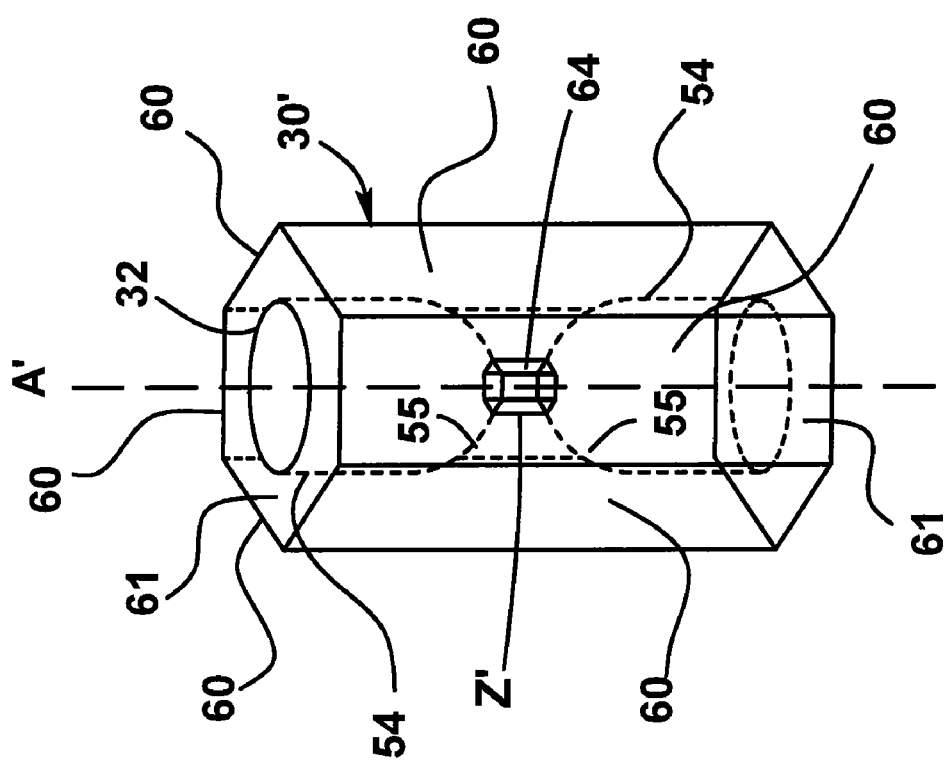
FIG. 5 is a perspective illustration of a monolithic six-sided optical flow cell that is readily made by the manufacturing method of the invention and is useful in another embodiment of the FIG. 1 instrumentation.
Figure 6:
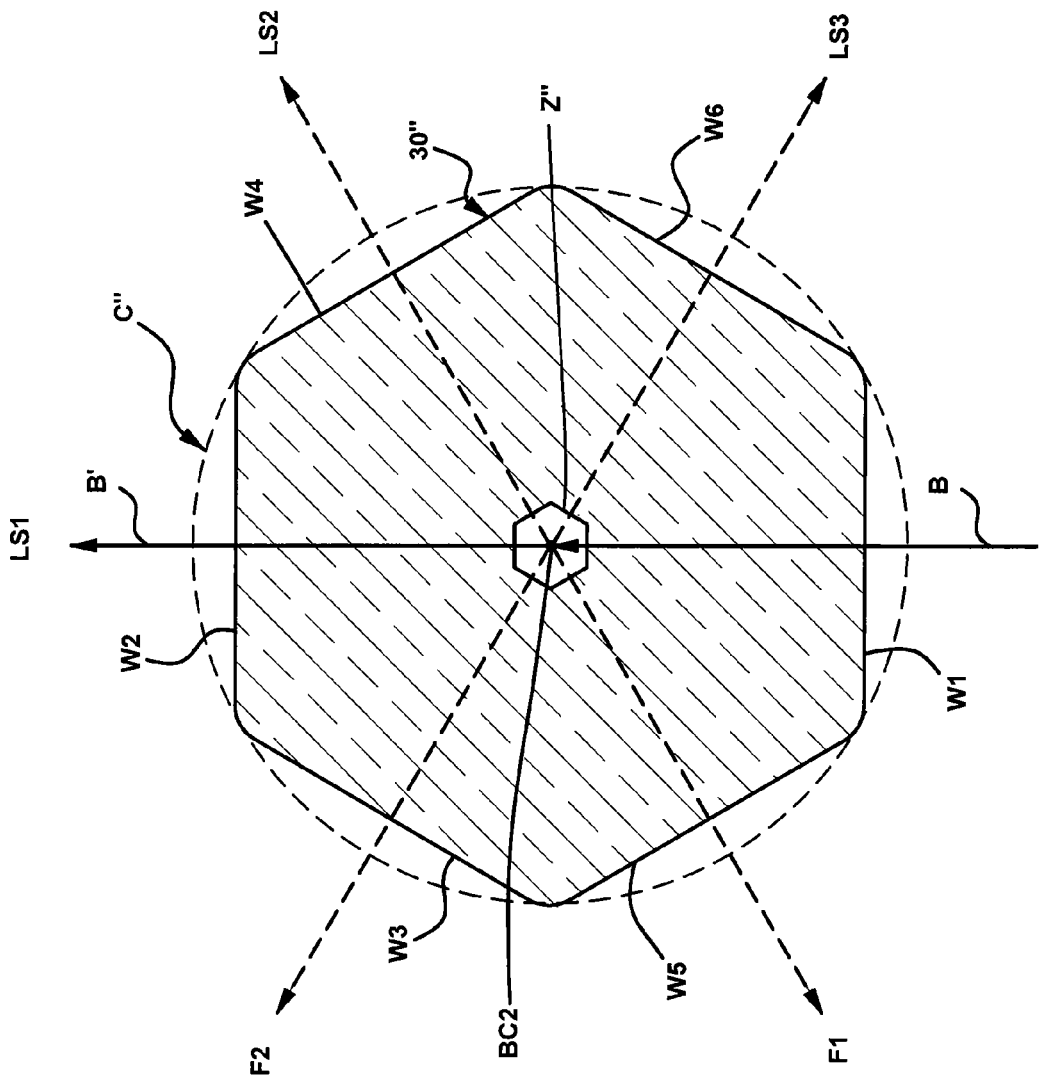
FIG. 6 illustrates a hexagonal optical flow cell and a manner of use.
Figure 7:
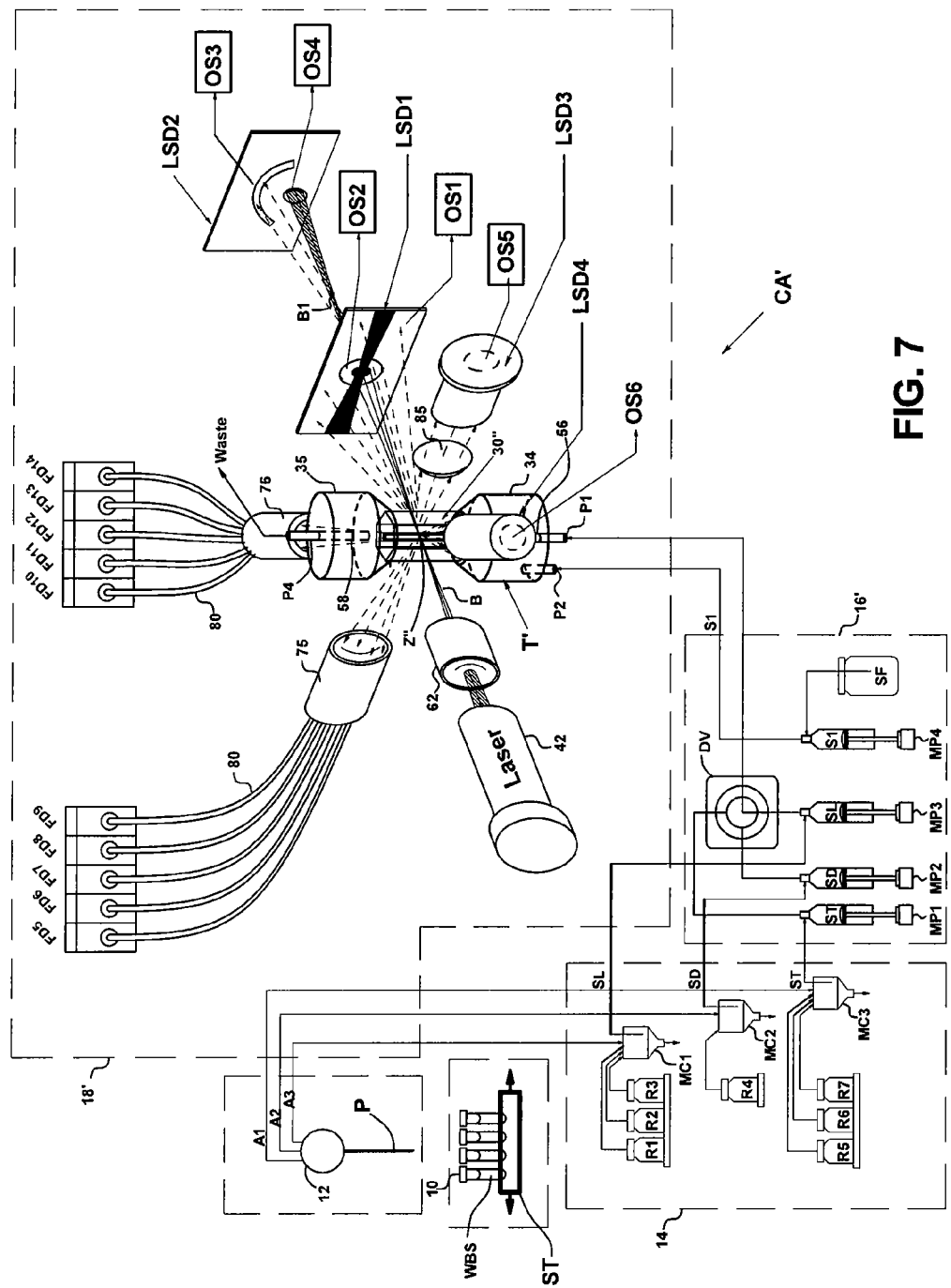
FIG. 7 is a schematic illustration of the sample-processing and data-acquisition portions of a flow cytometer that relies solely on optical properties of formed bodies to differentiate subpopulations of same, in which distinguishing parameters are acquired from formed bodies transiting the hexagonal flow channel illustrated in FIG. 6.

FIG. 5 illustrates another monolithic optical flow cell 30' adapted for use in other embodiments of the FIG. 1 instrumentation. Like FIG. 1 flow cell 30, FIG. 5 flow cell 30' is made from a single piece of a seamless transparent material, most preferably synthetic amorphous silica ($SiO_2$). A central particle-sensing zone Z', of transverse cross-section bounded by six planar surfaces 64, extends for about 70 micra along the longitudinal axis A' of flow cell 30'. The envelope of flow cell 30' is also prismatic in form, being bounded by six lateral sides 60 of rectangular shape, and a pair of opposing planar end surfaces 61 of hexagonal shape. Preferably, the respective transverse hexagonal cross-sections of particle-sensing zone Z' and the envelope of flow cell 30' are substantially similar and coaxial, the six planar surfaces 60 defining the lateral boundary of said envelope being arranged substantially parallel to the respective six planar surfaces 64 of particle-sensing zone Z'. Said transverse cross-sections being thus arranged, six walls of predetermined uniform thickness and forming flat windows are provided for introducing a beam of radiation into particle-sensing zone Z' and for coupling such radiation out of the said particle-sensing zone after interaction with formed bodies passing seriatim through it. Opposing planar end surfaces 61 are similarly coupled into the supporting fluidic circuit as was described for end surfaces 36 of FIG. 1 flow cell 30. In FIG. 6 a transverse cross-section through the particle-sensing portion of the sample passageway in a six-sided optical flow cell 30" is shown; thus, FIG. 6 is equally representative of a purely optical flow cell having a uniform prismatic flow channel or one enabling acquisition of both optical and Coulter parameters within a portion of such channel forming a volumeter conduit. Here, a laser beam B passes through window W1 to irradiate a formed body FB passing through the particle-sensing zone Z" in a direction perpendicular to the plane of the drawing. Absorbance (A) of beam B by the irradiated formed body FB is determined from the intensity of the partially absorbed beam B' passing through window W2, e.g., by the OS4 portion of FIG. 1 photo-detector LSD2. Forward light scattered by the irradiated formed body is measured at two different angles (LS1 and LS2) through windows W2 and W4, e.g., LS1 through window W2 by one or more photoactive regions OS1, OS2, and OS3 of FIG. 1 photo-detectors LSD1 and LSD2; and LS2 through window W4 by suitably-located photoactive region OS1 of FIG. 1 photo-detector LSD3. Fluorescence radiation emitted at different wavelengths may be measured through one or more of the remaining windows W3, W5, and W6 via complete or partial replications of the FIG. 1 collection and wavelength-separation network for fluorescence described in connection with the FIG. 1 embodiment. However, in many applications requiring fluorescence measurements such elaboration is not needed and, via the additional sides to the internal sensing zone and envelope of flow cells such as shown in FIGS. 5 and 6, multiple fluorescence parameters can be measured separately through a dedicated window, thus avoiding the practical complications due to serial beam-splitters BS1 and BS2 in the fluorescence detection path shown in FIG. 1. In such embodiments, F1 and F2 are measured through windows W3 and W5 respectively, e.g. by suitably-located replications of FIG. 1 lens 51, lens assembly 70, filter 73, and fluorescence detector FD3, but without BS1 and BS2 in the optical path. Light at low back-scattering angles is shown exiting window W6 but, if preferable, fluorescence radiation at a third wavelength could be measured though this window by a replication of FIG. 1 lens 51, lens assembly 70, filter 73, and fluorescence detector FD3. One such embodiment, for clarity of illustration relying solely on optical parameters, is illustrated in FIG. 7, where labels repeated from FIG. 1 have identical meanings and functions as indicated in discussion related thereto. In such applications absence of a volumeter conduit makes adequate post-analysis sample flushing easier to achieve, so in addition to FIG. 1 Coulter sensing electrodes 38 and 40 and RF/DC circuit 41, second sheath S2, its pump MP5, and associated ports P3, P5, and P6 in cap elements 34 and 35 of transducer assembly T do not appear in FIG. 7. In the latter figure, laser excitation beam B from laser 42 and beam-shaping optics 62, or their fiber-coupled beam-shaping equivalent, enters one window of hexagonal monolithic optic flow cell 30" and exits a second window opposite the first, after being scattered by formed bodies in prismatic flow channel Z". Such forward-scattered light is intercepted by photo-detectors LSD1 and LSD2 as described for the FIG. 1 embodiment, so producing analogous forward-scattered (FS) signals. Fluorescence radiation emitted by fluorescent moieties on or within the formed bodies (F1 and F2 in FIG. 6) is intercepted by at least one of suitably-located fiber-optic collection modules 75 and 76 through a third window (W3 or W5 in FIG. 6) and coupled to fluorescence detectors FD5-FD14 in FIG. 7 via fiber optics 80; alternatively, such fluorescence interception and conversion to electrical signals may be accomplished with free-space optic coupling such as illustrated in FIG. 1, appropriately located to efficiently collect emitted fluorescence. Low-angle side-scattered light (LS2 through a fourth window W4 in FIG. 6) may be intercepted by suitably-located FIG. 7 collection lens 85 and photo-detector LSD3 for conversion by the photoactive region OS5 of the latter into a side-scatter (SS) signal. Similarly, low-angle back-scattered light (LS3 through a fifth window W6 in FIG. 6) may be intercepted by a suitably-located combination of a collection lens (not shown, to minimize confusion) and FIG. 7 photo-detector LSD4 for conversion by the photoactive region OS6 of the latter into a side-scatter (SS) signal; if preferable, fluorescence radiation at a third wavelength could instead be measured though this window by a third suitably-located fluorescence collection and transduction arrangement such as described above. It is understood that directly back-scattered light could be measured through FIG. 6 window W1 in much the same manner as described above for the embodiment in FIG. 1. For applications requiring transduction of Coulter parameters, flow cell 30" must comprise a suitable passageway including appropriate bores 54 and surfaces of revolution 55 as shown for flow cell 30' in FIG. 5; in addition, transducer assembly T' will require FIG. 1 electrodes 38 and 40 connected to DC/RF circuit 41, sheath S2 and pump MP5, and ports P3, P5, and P6; all said components function as described for the exemplar embodiment illustrated in FIG. 1. It is understood that embodiments according to FIG. 7, but suited to particular applications, may benefit from having either more or less than the six windows illustrated therein, i.e., monolithic optical flow cells having similar transverse polygonal cross-sections through the particle-sensing portion of their sample passageways and their envelopes aligned as described but having, e.g., three, five, seven or eight windows. While conventional assemblage of planarized plates or truncated pyramids to provide optical flow cells as described in the present paragraph would be virtually impossible, truly monolithic flow cells for both purely optical transducers and combined optical and Coulter transducers can be provided by the glass-drawing technique described below.

To manufacture a seamless, monolithic optical flow cell of the type described above with reference to FIGS. 2-6, it is preferred to use a modified version of the glass-drawing technique presently used to produce thick-walled cylindrical flow cells having a flow channel of circular cross-section such as used in Coulter® Model LH750 hematology analyzers made and sold by Beckman Coulter, Inc. As noted in the introductory portion of this application, it is known in the glass-working art to draw cylindrical tubing from a larger preform of various inner and outer diameters between which is a cylindrical wall up to several centimeters in thickness. The required wall thickness is attained by sliding over, heating, and collapsing onto a first tube made of a form of silica ($SiO_2$) a second larger such tube (a sleeve tube) and fusing the second tube to the first tube, so seamlessly increasing the wall thickness of the preform; such oversleeving step is repeated with additional sleeves of appropriate increasing inner and outer diameters until the fused structure so formed has the required wall thickness to yield the desired flow-cell wall thickness after the preform is drawn to provide the desired cross-sectional area in the cooled drawn monolithic structure. During the drawing process, the preform is heated to a predetermined temperature at which its viscosity permits deformation, whereupon it is drawn axially, usually in a vertically downward direction in a conventional drawing tower, at a constant and predetermined rate. During this process, the diameters of the inner and outer cross-sections of the preform are substantially reduced with the original circular shapes being substantially retained and the wall of the preform being significantly reduced in thickness. It is understood that the drawing process also acts to further improve the mechanical integrity of fusion interfaces formed during the aforesaid oversleeving process, whereby mechanical properties of the resulting monolithic structure closely approach those of the bulk material from which were made the various tubes used in such process. Retention of circular cross-sections is a relatively simple matter since such cross-sections are the minimum-energy shape inherent in such preform-drawing processes. Maintaining a non-circular cross-section during such drawing process, particularly of the critical polygonal internal flow channel as required to produce the above-described optical flow cells, is not at all straight forward.

The manufacturing method of the invention begins with the production of a suitable preform, one yielding after the drawing operation the desired geometry for the particle-sensing zone and sufficient wall thickness to allow fabrication of the desired flow-cell envelope. Such preform comprises a tube of transparent siliceous material (e.g., silica, or more preferably synthetic amorphous silica, $SiO_2$) having an axially-extending channel exhibiting a substantially uniform transverse cross-section of a desired polygonal shape, e.g., triangular, rectangular, or hexagonal. Said channel cross-sectional shape is achieved by inserting a mandrel of appropriate transverse cross-section into a tube of the siliceous material and heating the tube to cause it to collapse onto the mandrel, thereby causing the tube to assume the mandrel shape throughout the rectilinear internal channel so formed. As noted above, the wall of the preform must be such as to yield a flow-cell envelope having a desired wall (or window) thickness after the preform has been sufficiently drawn to achieve the desired cross-sectional area of the interior channel. To facilitate fabrication of envelopes comprising planar surfaces, before drawing the preform is finished by preferably having at least one reference flat prepared on its outer surface that is substantially parallel to one of the planar sides defining its interior channel. After drawing, such reference flat is used to align the drawn structure for subsequent conventional machining operations required to provide and finish the desired flow-cell envelope and, if Coulter V and/or C parameter are to be simultaneously acquired in the particle-sensing zone of the flow cell, the longitudinal section required for adequate characterization of formed bodies by the Coulter Principle.

Figure 8B:
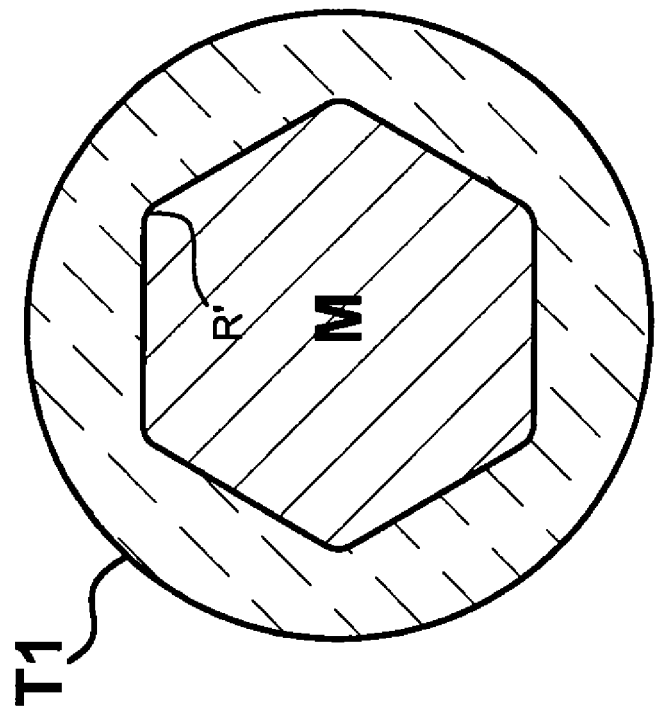
FIGS. 8A and 8B illustrate two steps of a preferred process for making a preform that is useful in the manufacturing method of the invention, i.e., of the type used in producing the monolithic optical flow cells of the invention.
Figure 8A:
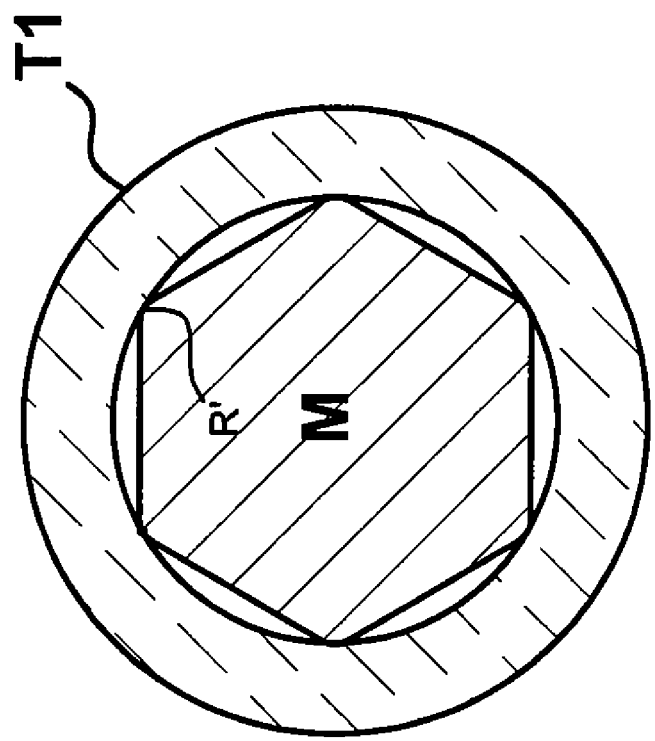

Referring to FIGS. 8A and 8B, production of a useful preform requires a mandrel M of a suitable metal alloy, e.g., steel, machined to have a transverse cross-section similar to that of a desired particle-sensing zone, e.g., Z or Z' in respective FIGS. 1-4 and FIG. 5. As indicated in FIGS. 8A and 8B, for some desired geometries a small radius R' on corners of mandrel M may be beneficial. A cylindrical tube T1 of the desired siliceous glass, most preferably synthetic amorphous silica, is then appropriately cleaned and, as shown in FIG. 8A, slid onto said mandrel, the tube with the mandrel within it then being mounted on a lathe and rotated. As is known in the glass-working art, heat is applied to the tube until the glass reaches its softening temperature and its viscosity is in the range of $1 \times 10^6$ poise to $60 \times 10^6$ poise, more preferably between $3 \times 10^6$ poise and $28 \times 10^6$ poise, whereby the softened tube can be collapsed onto the mandrel and the interior cross-section of the tube is caused to take the shape of the mandrel, as shown in FIG. 8B. Preferably, after appropriate cooling, the mandrel is removed from the collapsed tube, but may less preferably be left in said tube during part of or all of a subsequent oversleeving process. The external cross-section of the preform must be sufficient that, after the tube is drawn to provide the desired channel cross-sectional area, the desired flow-cell envelope may be fabricated, e.g., in FIG. 6, C" is the boundary of the maximum cross-sectional area leaving a beneficial non-sharp corner on flow cell 30" after the flats forming the outer surfaces of windows W1-W6 are polished onto a segment of the drawn preform. To achieve the necessary thickness of the preform walls, a second appropriately sized glass tube (a sleeve tube), preferably of the same glassy material as the first, is slid over the first tube, and said combination is rotated on a lathe and heated to achieve viscosity within the aforesaid range. At such viscosity, the second tube collapses onto the first tube and the siliceous materials fuse together to form a monolithic tube having a thicker wall. This process is repeated as necessary to achieve the required external cross-section for the desired flow cell, whereon the fused structure is cooled. For flow cells 30 and 30' in respective FIGS. 2 and 5, a preferred cross-sectional preform ratio (mandrel area/envelope area) is between $0.4 \times 10^{-4}$ and $5.1 \times 10^{-4}$, and most preferably about $1.5 \times 10^{-4}$. For the aforesaid exemplar flow cells, the tubes used in making the preform have an inner diameter (ID) in the range between 2 and 40 mm, or preferably between 6 to 20 mm, and an outer diameter (OD)

in the range between 6 and 55 mm, or preferably between 15 and 35 mm. The preform is preferably built up from silica tubes that are preferably made from silica synthesized through a chemical vapor deposition process or a sol gel process. The chemical impurity level of the silica is preferably less than 2600 ppm. Among other advantageous properties such silica has exceptional transmission in the 250 to 400 nm wavelength range and very low intrinsic fluorescence. The silica glass may also contain dopants, e.g., Ge, P, F, B, Yb, or Ti. Total dopant concentrations may vary up to 10% by weight. These dopants are useful to adjust optical properties of the silica, e.g. refractive index, absorbance, or fluorescence and physical properties such as softening point, strength, and stress distribution. Compared to other silicate glasses, synthetically fabricated silica glass also has very good chemical resistance, low coefficient of thermal expansion, and very low defect concentration. The drawn silica structure resulting from the above-described fabrication process has superior mechanical strength as compared to such structures fabricated from other glass types.

It will be understood that the above-noted ratios and preferable dimensions apply to a preferred process for making monolithic optical flow cell 30 of FIG. 2 or 30' in FIG. 5 having, respectively, square or hexagonal particle-sensing zones Z or Z' about 50 micra flat-to-flat, with wall thickness to permit proper finishing after drawing. Both monolithic flow cells were provided an envelope comprising optically polished planar surfaces having opposing flat separations of 4.2 mm, with respective widths of 4.2 .mm and 2.4 mm and lengths of 6.3 mm. Both flow cells have been demonstrated to function in appropriate flow-cell assemblies to which the FIG. 1 apparatus was adapted. While the respective sides of particle-sensing zones and envelopes such flow cell can be of the same width as was the case for the exemplar flow cells, i.e., said cross-sections are regular, sides can be of a width adapted to achieve a desired angular or optical path-length relationship between the flow axis within the particle-sensing zone and envelope sides, whereby efficient coupling to appropriate optical sensors may be provided. Those skilled in the glass-working arts can adapt these teachings to provide sensing zones and wall thicknesses appropriate to other intended applications. Larger cross-sectional areas in such monolithic optical flow cells require different ratios and/or larger preform ODs, and thicker walls require larger preform ODs. By appropriately adapting the ratios and dimensions, it is possible to form optical elements having channels of more than 62,500 micra$^2$ in cross-sectional area that provide acceptable optical data (S and F) in a flow cytometer or wall thicknesses up to 4.5 mm that provided usable V, C, and S data in conventional hematology analyzers.

Prior to drawing, it is preferred that the outer surface of the aforesaid preform have at least a single reference flat (e.g., to yield a flat about 1.85 mm in width after drawing) formed thereon by a conventional grinding process, such flat being acceptably parallel (e.g., within approximately 1 degree) to one of the internal flats; if desired, such additional flats may be ground parallel to each of the planar surfaces forming the internal polygonal channel. The flatted preform is then positioned in a vertical drawing tower where it is heated, by conventional means, to a predetermined softening temperature at which its viscosity permits deformation, and it is vertically drawn downward at a controlled rate, preferably between 0.05 and 2 meters/minute, for a controlled time and at a constant angular orientation, whereby the polygonal cross-sectional shape of the internal channel is maintained during the drawing operation and the desired cross-sectional area of reduced size is achieved in the cooled channel. After cooling the drawn tubular structure and cutting it to a desired length, the outer surface of such structure is lapped to provide additional planar reference surfaces, e.g., preferably extending substantially parallel to each of the flats of the internal flow channel, whereby the outer surface of the drawn structure will have a polygonal cross-section that is similar in shape to the interior channel and is substantially coaxial therewith. Note, as shown in FIG. 6, it is not necessary that all of the original cylindrical surface C''' of the optical element be removed in the flatting operations, i.e., exterior flats corresponding to some interior flow channel flats may not be provided or the required wall thickness for some windows may leave adjoining remnants of the original preform surface. Alternatively, the preform can be designed and sized so that the desired optical portions of the envelope can be attained while advantageously leaving such remnants: particularly for triangular and square flow-cell envelopes, truly planar surfaces extending to intersection form a corner sufficiently sharp as to be suffer edge chips during normal handling, and so are typically beveled as shown for the corners of flow cell 30 in FIG. 10 fabricated according to the present invention and flow cell 30 in FIG. 13 fabricated according to the prior-art planarization process. The need for such beveling step may be eliminated if the preform is designed to leave a small remnant of the original surface on the corners of the finished flow cell, as shown for flow cell 30'' in FIG. 6.

A preferred method for differentiating formed bodies using the flow cell of the invention comprises the steps of (a) providing a flow cell of the type described herein that comprises a joinless (i.e., seamless), monolithic, transparent material including an internal flow channel of polygonal transverse cross-section and having at least three discrete walls (windows) through which optical parameters can be sensed; (b) passing formed bodies through the polygonal flow channel while irradiating such formed bodies with a beam of radiation passing through one of such walls; and (c) detecting different optical parameters of the irradiated formed bodies through the other two walls. More preferably, such flow cell has at least five discrete walls (windows) through which optical parameters can be sensed and, upon irradiating formed bodies within the flow channel with a beam of radiation passing through a first wall, detecting forward-scatter radiation from the irradiated formed bodies through a second wall; detecting back-scattered radiation from the irradiated formed bodies through a third wall; detecting fluorescence characteristics of the irradiated formed bodies through a fourth wall; and detecting side-scattered radiation from the irradiated formed bodies through a fifth wall. Preferably, at least some of the aforesaid optical measurements are combined with Coulter volume V and conductivity C measurements simultaneously made on the irradiated formed bodies passing seriatim through the flow channel to differentiate such formed bodies.

From the foregoing description, it will be appreciated that a new and improved optical flow cell has been provided. Being comprised of a monolithic structure, all of the above-note drawbacks of multi-component devices are eliminated. Due to the elimination of joins inherent to composite flow cells made by assembly of complementary components, e.g., CC1-CC4 in prior-art flow cell 30 in FIG. 13, yields are dramatically improved during post-draw machining processes needed to form a desired flow-cell envelope and volumeter conduits suited to acquisition of Coulter V and/or C parameters, such as Z in FIG. 2 or Z' in FIG. 5. In addition, failure rates during use are reduced, and formed bodies are more readily differentiated. Further, the method of manufacture used to provide the exemplar flow cells is generally applicable to manufacture of a broad variety of optical flow-cell embodiments.

Figure 9:
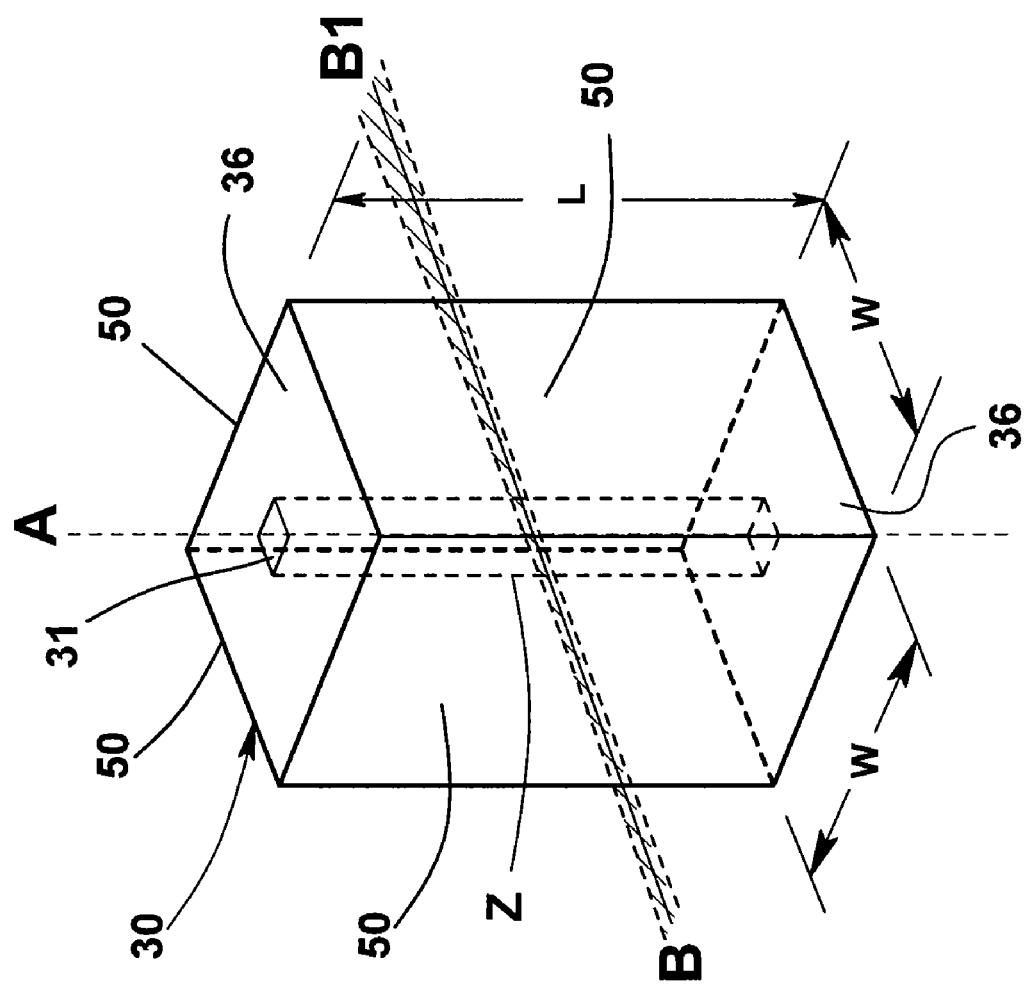
FIGS. 9 through 12A-12C illustrate other embodiments of monolithic optical flow cells made by the method of the invention.

FIG. 9 is a perspective illustration of a monolithic four-sided optical flow cell 30 that is fabricated by the method of the invention and is useful in an embodiment of the FIG. 1 instrumentation that relies solely on optical properties of formed bodies to differentiate subpopulations, in which distinguishing parameters are acquired from formed bodies transiting the square flow channel illustrated in FIG. 4 and passing seriatim through laser beam B. Such monolithic flow cells have been made by the above-described method that have square flow channels 31 of 47, 52, 65, 75, 100, 140, or 250 micra between their planar channel surfaces and square envelopes of 2.4, 3.5, or 4.2 mm width W between the planar exterior surfaces 50 lapped parallel to the internal channel surfaces; envelope lengths L of 6.3, 9.2 or 12.5 mm between end surfaces 36 have been provided. One such flow cell, having channel dimensions of 52 by 52 micra and envelope widths of 4.2 mm and length of 6.3 mm, is further processed into the exemplar flow cell 30 in FIG. 2 and used in the newly introduced Unicel® DxH hematology analyzer made and sold by Beckman Coulter, Inc. Another such flow cell, having channel dimensions of 250 by 250 micra and envelope widths of 4.25 mm and length of 12.7 mm, has been experimentally demonstrated in the XL™ fluorescence flow cytometer, also made and sold by Beckman Coulter, Inc.

Figure 10:
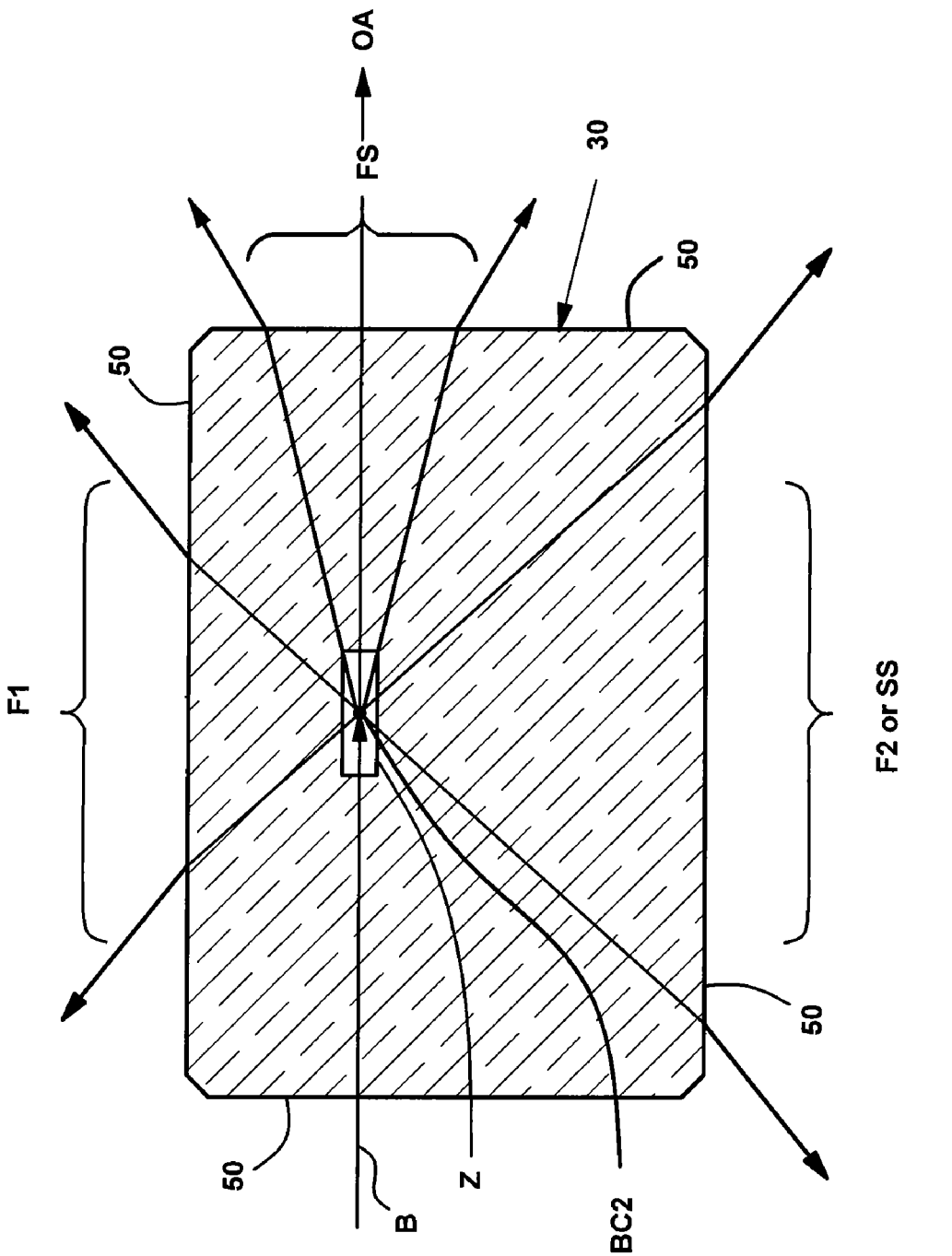

FIG. 10 illustrates a cross-sectional view through the particle-sensing zone Z of a monolithic four-sided optical flow cell 30 fabricated by the method of the invention and useful in an embodiment of the FIG. 1 instrumentation that relies solely on optical properties of formed bodies (e.g. BC2) to differentiate subpopulations, e.g., the FC500 fluorescence flow cytometer made and sold by Beckman Coulter, Inc. In this embodiment optical parameters are acquired from formed bodies transiting a rectangular flow channel located off the flow-cell axis. Experimental prismatic channels 140 by 320 micra have been made by the method of the invention, in a flow cell envelope defined by exterior planar surfaces 50 providing two sides of width 3.6 mm and two sides of width 5.0 mm. In such flow cells a thin window permits collection of fluorescence radiation, excited by laser beam B, up to the critical angle determined by the difference of refractive index across the glass/air interface with smaller collection optics, such as lens 51 in FIG. 1, of lesser cost than needed with typical flow-cell wall thicknesses. Forward scatter (FS) signals or other optical parameters [e.g., a second fluorescence (F2) signal or a side-scatter (SS) signal] may be acquired in the conventional manner.

Figure 11:
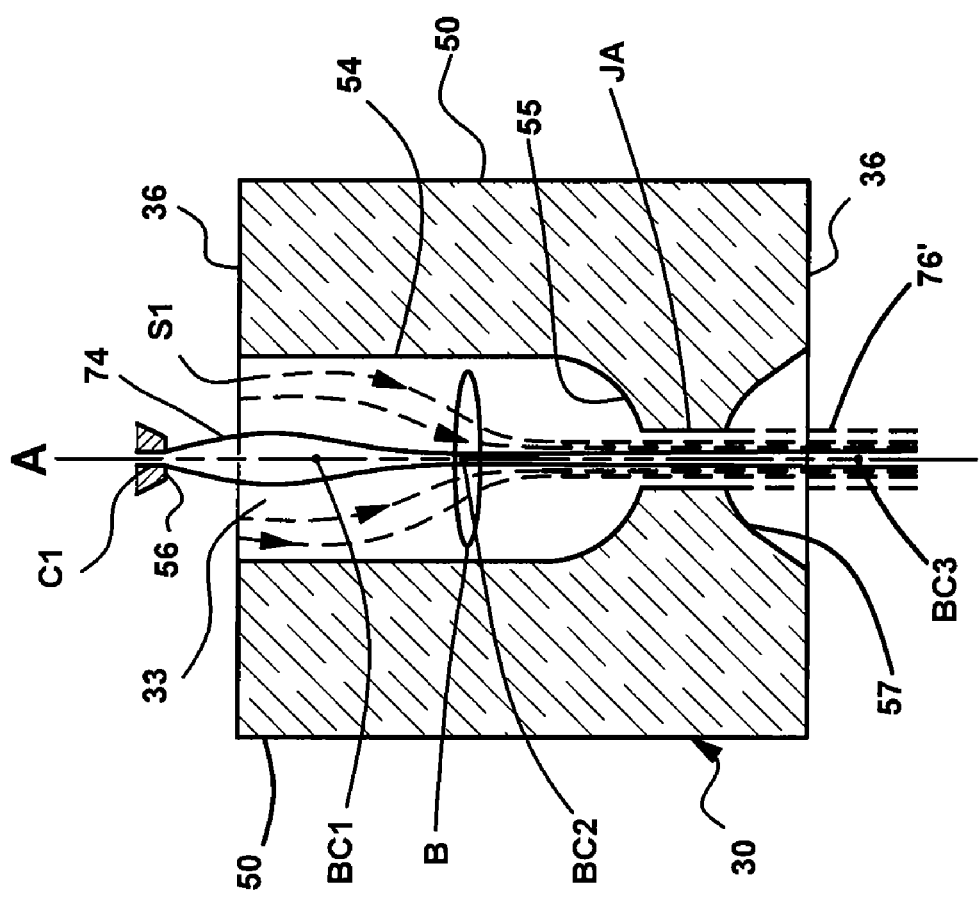

FIG. 11 illustrates a longitudinal section through the jetting aperture JA of a monolithic optical flow cell 30 fabricated from the monolithic flow cell 30 in FIG. 9 via methods used to form the volumeter conduit Z of flow cell 30 in FIG. 2. This embodiment is useful in a flow cytometer that relies solely on optical properties of formed bodies (e.g., BC1-BC3) passing seriatim through laser beam B to differentiate and sort selected subpopulations according to their distinguishing parameters. Items in FIG. 11 labeled identically to ones in FIG. 2 function in like manner, i.e., sample stream 74 is projected toward JA by channel C1 in nozzle 56 and is surrounded by sheath liquid S1 in passageway 33 as has been described. Passageway 33 differs from FIG. 2 passageway 32 in having a longer bore 54 through upper end surface 36, so that the portion of original square channel forming jetting aperture JA is located close to the lower end surface 36, which is unattached to instrument fluidics. Jetting aperture JA is 75 by 75 micra and about 500 micra long between surfaces of revolution 55 and 57 and within a square envelope comprising planar surfaces 50 that are 2.4 mm wide by 6 mm long. Composite stream 76' of outer sheath and central sample streams exits through jetting aperture JA to form a jet in air. Drops containing desired formed bodies can then be electrostatically deflected in the conventional manner according to the parameters sensed by conventional optical transduction methods. Although laser beam B is shown intersecting the sample stream above jetting aperture JA, it may be advantageous in some applications to couple the laser beam B through the flow-cell wall surrounding the aperture as described for the FIG. 1 instrumentation, so that optical sensing occurs within the jetting aperture itself.

Figure 12C:
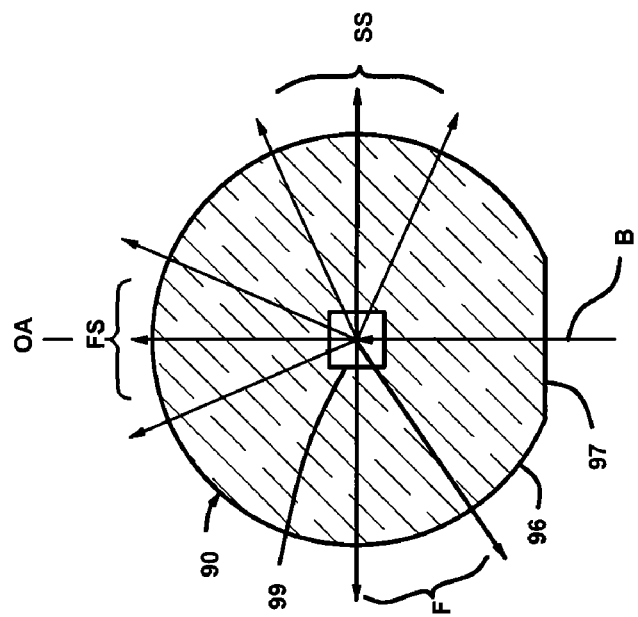
Figure 12B:
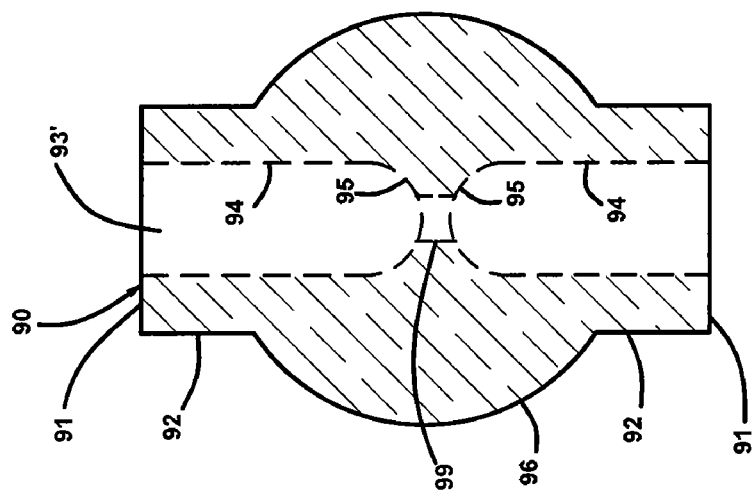
Figure 12A:
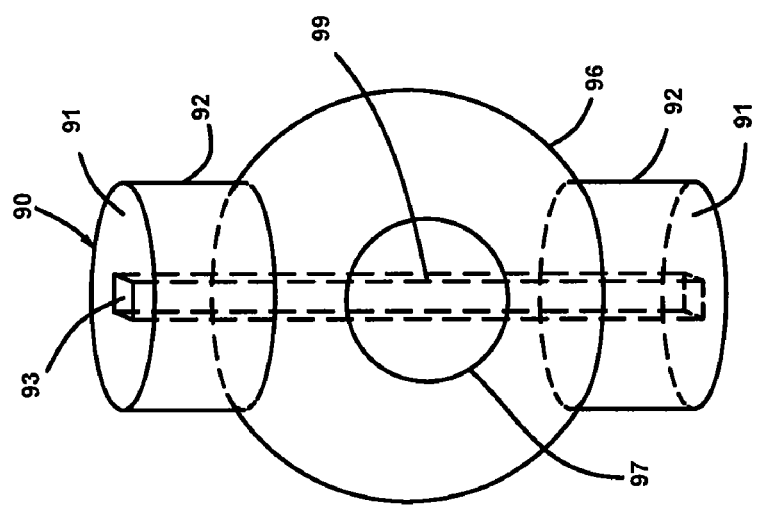
Figure 13:
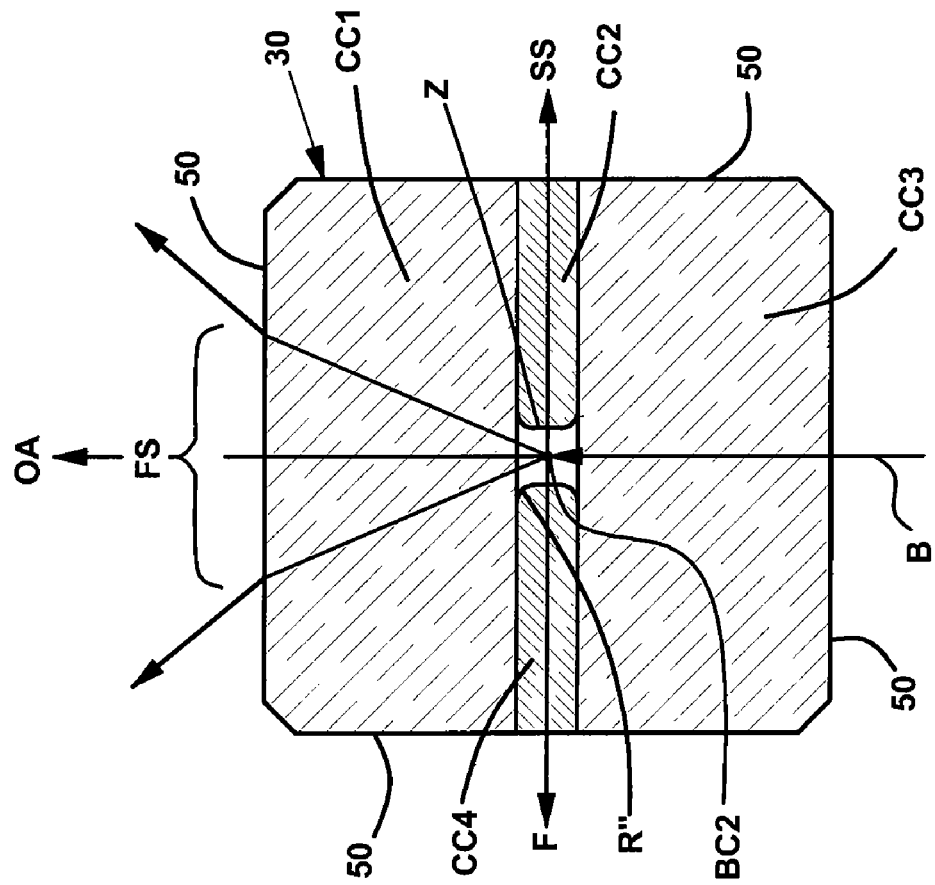
FIG. 13 illustrates a cross-sectional view through the particle-sensing zone of prior-art flow cells of the type in FIGS. 2 and 9, the FIG. 2 flow cell being fabricated from the latter.

FIGS. 12A, 12B, and 12C illustrate different aspects of an monolithic optical flow cell 90 fabricated by grinding and polishing an envelope having a central non-cylindrical surface of revolution 96, preferably coaxial with prismatic flow channel 93; beyond the desired surface of revolution, material is removed to form integral support cylinders 92, also coaxial with the axis of flow channel 93. Preferably, said surfaces are generated as known in the glass-working art by mounting a length of an appropriate drawn structure, made by the method above described and longer that the desired length of flow cell 90, between centers and removing the excess length to form end surfaces 91 once surface 96 is finished as required. Preferably, flat 97 for coupling a laser beam into the sensing portion 99 of flow channel 93 is made as a reference flat prior to drawing the preform, as has been described, and provided an optical polish once surface 96 is generated but before any excess length is removed to form end surfaces 91. FIG. 12A is a perspective view of such a flow cell 90 suited for use in instrumentation relying solely on optical parameters for differentiation of types of formed bodies. FIG. 12B illustrates an axial longitudinal section of a similar optical flow cell comprising a central volumeter conduit for simultaneous determination of both optical and Coulter V and/or C properties; made as was voltmeter conduit Z in FIG. 2, passageway 93' comprises bores 94 from end surfaces 91 and transition surfaces of revolution 95 from bores to volumeter conduit 99 in this figure. FIG. 12C is a transverse cross-section through the particle-sensing zone of the flow cell in FIG. 12A or 12B. Laser beam B enters flow cell 90 via flat 97 and interacts with formed bodies within particle-sensing zone 99. Due to the relatively small mismatch in refractive index between suspending liquids and silica, light scattered from laser beam B by formed bodies, or emitted from fluorescence moieties used to mark some population of formed body, will be slightly deviated as for flow cells having envelopes comprising planar windows on crossing the planar surface of flow channel 93 in FIG. 12A or volumeter conduit 99 of FIG. 12B. However, as shown in FIG. 12C, such light will not be refractively deviated on passing through the envelope formed by surface of revolution 96, whereas light similarly passing through an envelope comprising planar surfaces is refractively deviated according to the relatively large mismatch in index between silica and air as shown in FIGS. 4, 10, and 13. Consequently, flow cells such as 90 in FIGS. 12A and 12B offer greater collection efficiency and so advantages where low light levels must be sensed. Flow cells having a spherical surface of revolution 96 of radius 3.2 mm and a length of 9.5 mm between end surfaces 91 have been fabricated by the methods herein disclosed.

As noted in the introductory portion of this application, certain disadvantages are inherent in composite optical flow cells made by joining complementary components to achieve optical flow cells having a flow channel or volumeter conduit of polygonal transverse cross-section in which particle properties are sensed. It was also noted there how monolithic optical flow cells having a cylindrical flow channel and coaxial envelope, made as thick-wall tubing drawn from an oversize preform, avoid such disadvantages, but induce aberrations in optical parameters acquired through the wall surrounding the particle-sensing zone. The paragraphs immediately preceding this one describe how the present inventive method of flow-cell manufacture avoids the aforesaid disadvantages of composite flow cells and reduces the optical disadvantages of cylindrical flow cells. However, there are further significant advantages of particle-sensing zones having the polygonal cross-section comprised within truly monolithic optical flow cells of the type herein described. These advantages originate from the elimination of imperfections in the joins used to assemble composite flow cells having non-cylindrical flow channels or volumeter conduits such as described in the '652 patent or in U.S. Patent Application 2007/0085997 and its precursors. Such joins have been made via use of adhesives, low-temperature glass-bonding processes using chemical agents or solder glasses, or high-temperature fusion processes in which surfaces of the complementary components to be joined are placed in close proximity and heated sufficiently to cause those surfaces to soften and bond to each other. Joins formed by the first two methods are significantly less durable than those formed by fusion of the complementary components and may result in background fluorescence that interferes with the weak fluorescent radiation emitted by formed bodies transiting the resulting particle-sensing zone; in addition, the bonding agents may extend or leave a residue beyond the machined surfaces intended to define the corner geometry of the particle sensing zone and thus cause unpredictable unit-to-unit variability in fluid flow through the sensing zone. Alternatively, insufficient bonding agent may inadequately fill the gap between adjacent components of the composite flow cell, leaving a void extending between such components along the length of the corner these components were intended to form. Viscous forces acting on adjacent surfaces of non-cylindrical flow channels combine such that fluid flows near the corners experience additional resistance, and so slower flow velocities, than near the mid-portions of the surfaces. Consequently, formed bodies outside near-axial flow in non-cylindrical channels experience lower flow rates and may migrate into the corners of such flow channels, e.g., during flow transitions required for flushing of one sample from, and introduction of a different sample into, passageway 32 in FIGS. 2 and 3. Due to the small dimensions of volumeter conduits and the greater difficulty in thoroughly flushing them, this possibility is most worrisome when Coulter V and/or C parameters are acquired and, as described above, requires additional complexity in transducer assembly T of the FIG. 1 instrumentation. Typical formed bodies are at most several micra in dimension and thus can be sequestered in such interstices in imperfect joins during such transitions. On resumption of continuous flow the viscosity-induced low flow rates near channel corners may be insufficient to sweep all such sequestered cells out, allowing the potential carry-over of formed bodies from one sample into a subsequent sample. If such a sequestered formed body were of the rare cell types critical to diagnosis, it would not only be absent from the first sample, but could occur in a following normal sample. Misleading diagnostic information could result from the subsequent processing of parameters acquired from both samples, so carry-over of formed bodies from one patient sample into another patient sample raises serious regulatory and liability concerns. Because of the difficulty (discussed above) in flushing the small volumeter conduits required for sensing Coulter V and/or C parameters, instrumentation using composite flow cells comprising such conduits and including fusion joins is subject to the latter fault and its implications as well. It was noted regarding the aforementioned monolithic cylindrical flow cells that these were readily formed because the channel shape was the minimum-energy shape for the glass softened as is necessary for the drawing operation. Minimum-energy considerations also apply during joining of complementary components and result during the fusion operation in rounding of the intersection of the surfaces to be joined and the surfaces intended to form the non-cylindrical flow channel. Thus, for example, in flow cells such as used in the experimental instrumentation described in the '652 patent (e.g., flow cell 30 in FIG. 13), the edges of the two spacer plates (e.g., CC2 and CC4 in FIG. 13) soften and round over about a center within the spacer plates before the bulk glass softens sufficiently to bond the surfaces to be joined; such rounding is indicated for one such edge of CC4 by R" in FIG. 13, but applies to both such edges of spacer plates CC2 and CC4. As indicated in FIG. 13, the cross-section of the resulting volumeter conduit Z is not truly rectangular, but rather has imposed at said four corners interstices adjacent to the two window plates (e.g., CC1 and CC3 in FIG. 13) and extending back from the intended corner for several micra. Interstices extending more than 15 micra away from the flow channel and along much of the flow cell length have been observed in commercial planarized flow cells used in said '652 instrumentation; these have a perceptible radius of several micra at both corners of both spacer plates. Such interstices carry with them the aforesaid potential for carry-over of formed bodies. As shown in FIG. 4, in the truly monolithic optical flow cells of the present invention minimum-energy considerations result in the corners of particle-sensing portion Z of passageway 32 in FIGS. 2 and 3 having an internal radius R and planar surfaces, by which the possibility of interstices and attendant carry-over is eliminated along with the attendant regulatory and liability concerns. Such radiusing also reduces the portion of the channel cross-section responsible for the worst viscosity-induced slowing of channel throughflow, thereby also facilitating flushing of formed bodies in one analyzed sample before introduction of a different sample when such flow cells are used in the FIG. 1 instrumentation.

The invention has been described in detail while making reference to certain preferred embodiments. It will be appreciated, however, that various changes and modifications can be made without departing from the spirit of the invention and the scope literally defined by the appended claims. For example, although it is preferable that passageway 32 be central and located along the longitudinal axis A of optical element 30, some applications benefit from the passageway being neither central nor along said axis. For example, monolithic optical elements 30 have been made for use in flow cytometers that had a rectangular passageway offset toward one wall in order to improve efficiency of fluorescence collection or to better match the optical path length through the wall with available collection lenses.

What is claimed is:

1. A method for making a transparent, monolithic optical flow cell of the type used to characterize formed bodies passing through it, said optical flow cell having formed therein a prismatic internal flow channel defined by at least three intersecting substantially planar surfaces, whereby said prismatic internal flow channel has a transverse cross-section that is substantially polygonal in shape, said method comprising the steps of:
   (a) providing a monolithic glass preform comprising a glass tube having a central, axially-extending prismatic internal flow channel therethrough, said channel exhibiting a substantially uniform transverse cross-section of a desired polygonal shape;
   (b) heating said monolithic glass preform to a predetermined temperature above the softening temperature of said glass tube;
   (c) axially drawing said monolithic glass preform at a controlled rate, for a controlled time and at a constant angular orientation, to achieve a desired transverse cross-sectional area of said prismatic internal flow channel, thereby creating a drawn monolithic glass preform.

2. The method as defined by claim 1 wherein said glass tube comprises synthetic amorphous silica.

3. The method as defined by claim 1 further comprising the step of lapping a flat surface onto the outer surface of said glass tube prior to step (b), said flat surface being substantially parallel to one of the planar surfaces defining said prismatic internal flow channel.

4. The method as defined by claim 3 further comprising the step of cooling said drawn monolithic glass preform after step (c) and using said flat surface on the outer surface of said drawn monolithic glass preform as a reference surface to produce additional flat surfaces on said drawn monolithic glass preform that are parallel to the other planar surfaces defining the prismatic internal flow channel, whereby the outer surface of said drawn monolithic glass preform can be provided with a polygonal cross-section that is similar in shape to at least a portion of the prismatic internal flow channel and is substantially coaxial therewith.

5. The method as defined by claim 3 further comprising the step of forming a non-cylindrical surface of revolution on at least a portion of the outer surface of the drawn monolithic glass preform such that a residual portion of said flat surface provides a planar window in the surface of revolution.

6. The method as defined by claim 1 further comprising the step of forming a non-cylindrical surface of revolution on at least a portion of the outer surface of the drawn monolithic glass preform.

7. The method as defined by claim 1 wherein the said transverse cross-sectional area of the axially-extending prismatic internal flow channel in the glass preform is shrunk by a factor of at least 1000 during said drawing step.

8. The method as defined by claim 7 further comprising the step of sliding one or more additional glass tube onto a preceding glass tube to increase the preform wall thickness prior to the heating and drawing steps and, after each additional glass tube is so positioned, heating the monolithic glass preform and the one or more additional glass tubes above the softening temperature of the glass material, thereby fusing the glass tubes together to form a monolithic structure.

9. The method as defined by claim 1 wherein said monolithic glass preform is made by (a) sliding a glass tube onto an elongated mandrel having a desired polygonal cross-section, said glass tube having concentric internal and external transverse cross-sections of circular shape centered on a longitudinal axis, (b) heating said glass tube and mandrel assembly to a temperature above the softening temperature of the glass tube while simultaneously rotating said glass tube and mandrel assembly about the longitudinal axis of said glass tube, whereby the transverse cross-section of the glass tube interior conforms to the polygonal cross-section of said mandrel, and the cross-section of the glass tube exterior remains substantially circular, and (c) removing said mandrel from the glass tube interior.

10. An optical flow cell for use in a flow cytometer of the type adapted to characterize formed bodies on the basis of at least their respective optical properties, said flow cell comprising a seamless, monolithic structure of optically-transparent material, a portion of said monolithic structure defining a prismatic channel through which formed bodies can be made to pass while being irradiated by optical radiation passing through said monolithic structure, at least an axial portion of said flow channel having a transverse cross-section of polygonal shape, whereby optical radiation passing through said monolithic structure can irradiate formed bodies within said prismatic channel, and optical radiation resulting from said irradiation exits from said prismatic channel through different planar surfaces defining said prismatic channel, wherein the monolithic structure is formed from a monolithic preform comprising a glass tube having a central, axially-extending, prismatic channel having a substantially uniform transverse cross-section of a desired polygonal shape, and wherein the monolithic preform is heated and axially drawn to achieve a desired transverse cross-sectional area of said prismatic channel.

11. The optical flow cell as defined by claim 10 wherein said optically-transparent material comprises synthetic amorphous silica.

12. The optical flow cell as defined by claim 10 wherein said prismatic channel has three to eight sides.

13. The optical flow cell as defined by claim 10 wherein the outer surface of the monolithic structure is also prismatic in shape, with the number of prism sides being equal to the number of sides of the prismatic channel and substantially parallel thereto, whereby a plurality of flat windows is provided through which radiation can enter and exit the prismatic channel.

14. The optical flow cell as defined by claim 10 wherein the outer surface of the monolithic structure is provided with additional flat sides parallel to different sides of the prismatic channel, thereby providing a plurality of flat windows through which radiation can enter and exit the prismatic channel.

15. The optical flow cell as defined by claim 10 wherein at least a portion of the outer surface of the monolithic structure is circular in cross-section to enable radiation to exit the optical flow cell with minimal deviation due to refraction at the surface.

16. A method for differentiating formed bodies in a liquid sample comprising the steps of
(a) providing a seamless monolithic optical flow cell having at least three discrete planar walls defining a central flow channel of polygonal cross-section, the flow cell being formed from a monolithic glass preform having a central channel of polygonal cross-section that has been heated and drawn to form a central polygonal channel of desired cross-sectional area;
(b) passing formed bodies seriatim through the flow channel while irradiating such formed bodies with a beam of radiation passing through one of such walls;
(c) detecting different optical parameters of the irradiated formed bodies through at least two of said walls.

17. The method as defined by claim 16 wherein said monolithic optical flow cell has at least five discrete planar walls and wherein forward-scatter radiation from the irradiated formed bodies is detected through two of said walls, and fluorescence emitted from the irradiated formed bodies is detected through two other of said walls.

18. The method as defined by claim 17 wherein said light-scatter and fluorescence measurements are combined with Coulter volume V and/or conductivity C measurements simultaneously made on formed bodies passing seriatim through said central flow channel to further differentiate formed bodies.

19. The method as defined by claim 16 wherein said optical flow cell comprises synthetic amorphous silica.

\* \* \* \* \*